(12) United States Patent
Tozer et al.

(10) Patent No.: US 6,355,665 B1
(45) Date of Patent: *Mar. 12, 2002

(54) 1H-4(5)-SUBSTITUTED IMIDAZOLE DERIVATIVES, THEIR PREPARATION AND THEIR USE AS HISTAMINE $H_3$ RECEPTOR LIGANDS

(75) Inventors: Matthew John Tozer, London; Sarkis Barret Kalindjian, Banstead; Ian Duncan Linney, Guildford; Katherine Isabel Mary Steel, Beckenham; Michael John Pether, Orptington; Tracey Cooke, Royston, all of (GB)

(73) Assignee: James Black Foundation Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/463,012
(22) PCT Filed: Jul. 14, 1998
(86) PCT No.: PCT/GB98/02067
§ 371 Date: Mar. 14, 2000
§ 102(e) Date: Mar. 14, 2000
(87) PCT Pub. No.: WO99/05114
PCT Pub. Date: Feb. 4, 1999

(30) Foreign Application Priority Data

Jul. 25, 1997 (GB) ............................................. 9715814

(51) Int. Cl.$^7$ .................. C07D 233/54; A61K 31/4164
(52) U.S. Cl. .................. 514/400; 548/340.1; 548/342.1
(58) Field of Search ........................... 548/340.1, 342.1; 514/400

(56) References Cited

U.S. PATENT DOCUMENTS

| | | | |
|---|---|---|---|
| 3,444,175 A | 5/1969 | Shen et al. | 260/294.8 |
| 3,682,949 A | 8/1972 | Sarett et al. | 260/309 |
| 3,901,908 A | 8/1975 | Fitzi et al. | 260/309 |
| 3,953,460 A | * 4/1976 | Durant et al. | 260/294.8 G |
| 4,147,698 A | 4/1979 | Wade et al. | 260/301 |
| 6,080,871 A | * 6/2000 | Kalindjian et al. | 548/335.5 |

FOREIGN PATENT DOCUMENTS

| | | |
|---|---|---|
| DE | 2061489 | 7/1971 |
| FR | 2.227.869 | 11/1974 |
| GB | 1421792 | 1/1976 |
| WO | 93/14070 | 7/1993 |
| WO | 95/14007 | 5/1995 |
| WO | 96/29315 | 9/1996 |
| WO | 96/38142 | 12/1996 |
| WO | 97/29092 | 8/1997 |

OTHER PUBLICATIONS

Cornelis van der Stelt et al., "Synthesis and pharmacological properties of a series of , –diaryl–1H–imidazole–2–methanol derivatives,", European Journal of Medicinal Chemistry, vol. 13, No. 3, pp. 251–253, 1978, XP0002080033.

Jürgen Herke et al., "$H_2$–Antihistaminika, 3. Mitt.$^{1)}$–Synthese und $H_2$–antihistaminische Wirksamkeit Metiamid–analoger Sulfoxide und Sulfone.", Archiv der Pharmazie, vol. 312, pp. 35–39, 1979, XP002080034.

(List continued on next page.)

Primary Examiner—Floyd D. Higel
Assistant Examiner—Sonya Wright
(74) Attorney, Agent, or Firm—Foley & Lardner

(57) ABSTRACT

A compound of the formula (I)

Figure 1:
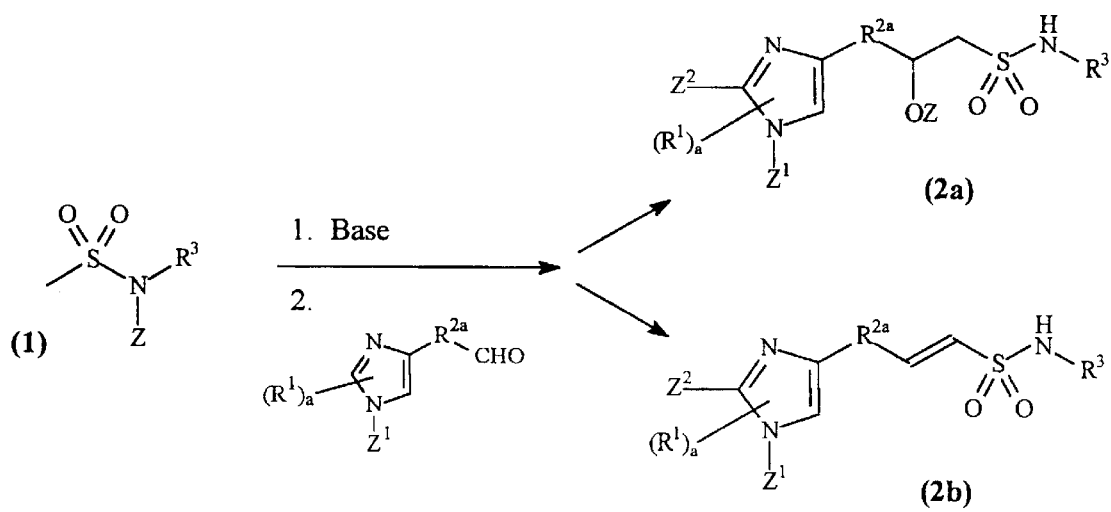

wherein $R^2$ is an optionally substituted $C_z$ to $C_g$ alkylene or alkylene chain; $R^3$ is $C_2$ to $C_{15}$ optionally substituted hydrocarbyl; X is a bond or —$NR^4$—, wherein $R^4$ is hydrogen or non-aromatic $C_1$ to $C_5$ optionally substituted hydrocarbyl, or aryl($C_1$ to $C_3$)alkyl, or a pharmaceutically acceptable salt thereof.

A method of modifying histamine activity in a patient comprising administering to said patient a pharmaceutical composition containing an effective amount of a compound of formula

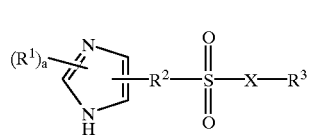

II wherein $R^1$ is selected from $C_1$ to $C_6$ alkyl, $C_1$ to $C_6$ alkoxy, $C_1$ to $C_6$ alkylthio, carboxy, carboxy($C_1$ to $C_6$)alkyl, formyl, $C_1$ to $C_6$ alkylcarbonyl, $C_1$ to $C_6$ alkylcarbonylalkoxy, nitro, trihalomethyl, hydroxy, amino, $C_1$ to $C_6$ alkylcarbonylalkoxy, nitro, trihalomethyl, hydroxy, amino, $C_1$ to $C_6$ alkylamino, di($C_1$ to $C_6$ alkyl)amino, aryl, $C_1$ to $C_6$ alkylaryl, halo, sulfamoyl and cyano; $R^2$ is optionally substituted $C_2$ to $C_{20}$ hydrocarbylene, in which one or more hydrogen atoms may be replaced by halogen atoms and up to 6 carbon atoms may be replaced by oxygen or nitrogen atoms, $R^2$ being in the form of an optionally substituted $C_2$ to $C_8$ alkylene or alkenylene chain; $R^3$ is hydrogen or $C_1$ to $C_{15}$ optionally substituted hydrocarbyl; X is a bond or —$NR^4$—; and a is from 0 to 2, or a pharmaceutically acceptable salt thereof.

4 Claims, 2 Drawing Sheets

OTHER PUBLICATIONS

James L. Kelley et al., "Inhibition of Histidine Decarboxylase by Imidazole Derivatives.", Journal of Pharmaceutical Sciences, vol. 70, No. 3, pp. 341–344, 1981, XP002080035.

Haruo Saikachi et al., "Synthesis of Furan Derivatives. LXXXVIII. [1)] Reactivity of Tosylmethyl Isocyanide towards Azole Carbaldehydes.", Chemical & Pharmaceutical Bulletin, vol. 30, No. 11, pp. 4199–4204, 1982, XP002080036.

Rodney C. Young et al., "Dipole Moment in Relation to $H_2$ Receptor Histamine Antagonist Activity for Cimetidine Analogues.", Journal of Medicinal Chemistry, vol. 29, No. 1, pp. 44–49, 1986, XP002089497.

Arthur A. Santilli et al., "Syntheses and Gastric Acid Antisecretory Properties of the $H_2$–Receptor Antagonist—N-[3-[3-(1-Piperidinylmethyl) phenoxy] propyl] thieno [3,4-d] isothiazol-3-amine 1, 1–Dioxide and Related Derivatives.", Journal of Medicinal Chemistry, vol. 31, No. 7, pp. 1479–1486, 1988, XP002089498.

Jacques Yves Gauthier et al., "Synthesis And Biological Evaluation of 2, 3–Diarylthiophenes As Selective Cox–2 Inhibitors. Part II: Replacing the Heterocycle.", Bioorganic & Medicinal Chemistry Letters, vol. 6, No. 1, pp. 87–92, 1996, XP002080037.

CT Supuran et al., "Carbonic anhydrase inhibitors. Pars 35*. Synthesis of Schiff bases derived from sulfanilamide and aromatic aldehydes: the first inhibitors with equally high affinity towards cytosolic and membrane–bound isozymes.", European Journal of Medicinal Chemistry, vol. 31, No. 6, pp. 431–438, 1996, XP004040067.

J.W. Clitherow et al., "Novel 1, 2, 4–Oxadiazoles As Potent And Selective Histamine $H_3$ Receptor Antogonists.", Bioorganic & Medicinal Chemistry Letters, vol. 6, No. 7, pp. 833–838, 1996, XP002089499.

* cited by examiner

1H-4(5)-SUBSTITUTED IMIDAZOLE DERIVATIVES, THEIR PREPARATION AND THEIR USE AS HISTAMINE $H_3$ RECEPTOR LIGANDS

This application is a 371 of PCT/GB98/02067 filed Jul. 14, 1998.

This invention relates to compounds which bind to histamine $H_3$ receptors, and to methods of making such compounds.

Histamine is well known as a mediator in certain hypersensitive reactions of the body, such as allergic rashes, hayfever and asthma. These conditions are now commonly treated with potent antagonists of histamine, so-called "antihistamines".

In the 1940s, it was noted that some physiological effects of histamine, such as increased gastric acid secretion and cardiac stimulation, were not blocked by the antihistamines which were then available. This led to the proposal that histamine receptors exist in at least two distinct types, referred to as $H_1$ and $H_2$ receptors. Subsequently, $H_2$ antagonists (such as cimetidine, ranitidine and famotidine) were identified, and they have become important in the treatment of gastric ulcers.

In the early 1980s, it was established that histamine also has a role as a neurotransmitter in the central nervous system. Arrang et al., Nature 302, 832 to 837 (1983), proposed the existence of a third histamine receptor subtype ($H_3$) located presynaptically on histaminergic nerve endings. Arrang et al. postulated that the $H_3$ receptor is involved in inhibiting the synthesis and release of histamine in a negative feedback mechanism. The existence of the $H_3$ receptor was subsequently confirmed by the development of selective $H_3$ agonists and antagonists (Arrang et al., Nature 327, 117 to 123 (1987)). The $H_3$ receptor has subsequently been shown to regulate the release of other neurotransmitters both in the central nervous system and in peripheral organs, in particular in the lungs and GI tract. In addition, $H_3$ receptors are reported to regulate the release of histamine from mast cells and enterochromaffin-like cells.

A need exists for potent and selective $H_3$ ligands (both agonists and antagonists) as tools in the study of the role of histamine as a neurotransmitter, and in its roles as a neuro-, endo- and paracrine hormone. It has also been anticipated that $H_3$ ligands will have therapeutic utility for a number of indications including use as sedatives, sleep regulators, anticonvulsants, regulators of hypothalamo-hypophyseal secretion, antidepressants and modulators of cerebral circulation, and in the treatment of asthma and irritable bowel syndrome.

A number of imidazole derivatives have been proposed in the patent literature as $H_3$ ligands. Representative are the disclosures of EP-A-0197840, EP-A-0214058, EP-A-0458661, EP-A-0494010, EP-A-0531219, WO91/17146, WO92/15567, WO93/01812, WO93/12093, WO93/12107, WO93/12108, WO93/14070, WO93/20061, WO94/17058, WO95/06037, WO95/11894, WO95/14007, U.S. Pat. Nos. 4,988,689 and 5,217,986.

According to the present invention, there is provided a compound of the formula

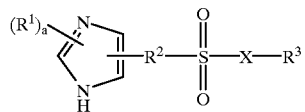

I wherein $R^1$ is selected from $C_1$ to $C_6$ alkyl, $C_1$ to $C_6$ alkoxy, $C_1$ to $C_6$ alkylthio, carboxy, carboxy($C_1$ to $C_6$)alkyl, formyl, $C_1$ to $C_6$ alkylcarbonyl, $C_1$ to $C_6$ alkylcarbonylalkoxy, nitro, trihalomethyl, hydroxy, amino, $C_1$ to $C_6$ alkylamino, di($C_1$ to $C_6$ alkyl)amnino, aryl, $C_1$ to $C_6$ alkylaryl, halo, sulfamoyl and cyano;

$R^2$ is $C_1$ to $C_{20}$ hydrocarbylene, in which one or more hydrogen atoms may be replaced by halogen atoms and up to 6 carbon atoms may be replaced by oxygen, nitrogen or sulfur atoms, provided that $R^2$ does not contain a —O—O— group, and provided also that the atom in $R^2$ which is linked to the —$SO_2$— moiety is a carbon atom;

$R^3$ is hydrogen or $C_1$ to $C_{15}$ hydrocarbyl, in which one or more hydrogen atoms may be replaced by halogen atoms and up to 3 carbon atoms may be replaced by oxygen, nitrogen or sulfur atoms, provided that $R^3$ does not contain a —O—O— group;

X is a bond or —$NR^4$—, wherein $R^4$ is hydrogen or non-aromatic $C_1$ to $C_5$ hydrocarbyl (in which one or more hydrogen atoms may be replaced by halogen atoms and up to 2 carbon atoms may be replaced by oxygen, nitrogen or sulfur atoms, provided that $R^4$ does not contain a —O—O— group), aryl($C_1$ to $C_3$)alkyl or $R^4$ represents a bond to $R^2$; and a is from 0 to 2 (preferably 0), and pharmaceutically acceptable salts thereof.

$R^2$ is preferably $C_1$ to $C_{15}$ hydrocarbylene, in which one or more hydrogen atoms may be replaced by halogen atoms and up to 4 carbon atoms may be replaced by oxygen, nitrogen or sulfur atoms, provided that $R^2$ does not contain a —O—O— group. More preferably, $R^2$ is $C_1$ to $C_8$ alkylene or alkenylene, optionally substituted by a hydroxyl group or an oxo group.

$R^3$ is preferably hydrogen, cycloalkyl($C_1$ to $C_3$)alkyl or aryl($C_1$ to $C_3$)alkyl. More preferably, $R^3$ is cyclohexyl($C_1$ to $C_3$)alkyl, adamantyl($C_1$ to $C_3$)alkyl, or phenyl($C_1$ to $C_3$)alkyl in which the phenyl group is optionally substituted by halo or methyl.

$R^4$ is preferably hydrogen or $C_1$ to $C_5$ alkyl. When $R^4$ represents a bond to $R^2$, it preferably forms a five- or six-membered ring, which may be fused to a ring system within $R^2$. For example, the moiety —$R^2$—$SO_2$—$NR^4$— may be an isothiazole dioxide group fused to six-membered carbocyclic ring. In the embodiment of Example 41 below, the moiety —$R^2$—$SO_2$—$NR^4$— is a 2,3,3a,4,5,7a-hexahydro-benzo[d]isothiazole 1,1-dioxide group.

The invention also comprehends derivative compounds ("pro-drugs") which are degraded in vivo to yield the species of formula (I). Pro-drugs are usually (but not always) of lower potency at the target receptor than the species to which they are degraded. Pro-drugs are particularly useful when the desired species has chemical or physical properties which make its administration difficult or inefficient. For example, the desired species may be only poorly soluble, it may be poorly transported across the mucosal epithelium, or it may have an undesirably short plasma half-life. Further discussion of pro-drugs may be found in Stella, V. J. et al., "Prodrugs", *Drug Delivery Systems*, pp. 112–176 (1985), and *Drugs*, 29, pp.455–473 (1985).

Pro-drug forms of the pharmacologically-active compounds of the invention will generally be compounds according to formula (I) having an acid group which is esterified or amidated. Included in such esterified acid groups are groups of the form —COOR$^5$, wherein R$^5$ is C$_1$ to C$_5$ alkyl, phenyl, substituted phenyl, benzyl, substituted benzyl, or one of the following:

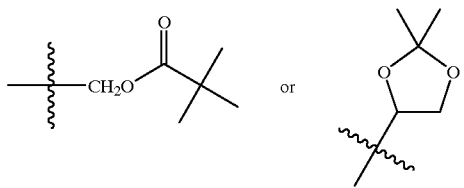

Amidated acid groups include groups of the formula —CONR$^6$R$^7$, wherein R$^6$ is H, C$_1$ to C$_5$ alky, phenyl, substituted phenyl, benzyl, or substituted benzyl, and R$^7$ is —OH or one of the groups just recited for R$^6$.

Compounds of formula (I) having an amino group may be derivatised with a ketone or an aldehyde such as formaldehyde to form a Mannich base. This will hydrolyse with first order kinetics in aqueous solution.

Pharmaceutically acceptable salts of the acidic compounds of the invention include salts with inorganic cations such as sodium, potassium, calcium, magnesium, and zinc, and salts with organic bases. Suitable organic bases include N-methyl-D-glucamine, benzathine, diolamine, olamine, procaine and tromethamine.

Pharmaceutically acceptable salts of the basic compounds of the invention include salts derived from organic or inorganic acids. Suitable anions include acetate, adipate, besylate, bromide, camsylate, chloride, citrate, edisylate, estolate, fumarate, gluceptate, gluconate, glucuronate, hippurate, hyclate, hydrobromide, hydrochloride, iodide, isethionate, lactate, lactobionate, maleate, mesylate, methylbromide, methylsulfate, napsylate, nitrate, oleate, pamoate, phosphate, polygalacturonate, stearate, succinate, sulfate, sulfosalicylate, tannate, tartrate, terephthalate, tosylate and triethiodide.

The compounds of the invention may exist in various enantiomeric, diastereomeric and tautomeric forms. It will be understood that the invention comprehends the different enantiomers, diastereomers and tautomers in isolation from each other, as well as mixtures of enantiomers, diastereomers and tautomers.

The term "hydrocarbyl", as used herein, refers to monovalent groups consisting of carbon and hydrogen. Hydrocarbyl groups thus include alkyl, alkenyl, and alkynyl groups (in both straight and branched chain forms), cycloalkyl (including polycycloalkyl), cycloalkenyl, and aryl groups, and combinations of the foregoing, such as alkylaryl, alkenylaryl, alkynylaryl, cycloalkylaryl, and cycloalkenylaryl groups. The term "hydrocarbylene" refers to corresponding divalent groups, the two free valencies being on separate atoms.

When reference is made herein to a carbon atom of a hydrocarbyl group being replaced by O, S or N, it will be understood that what is meant is that a —CH$_2$— group is replaced by —O— or —S—, or that

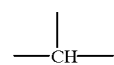

is replaced by

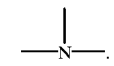

A "carbocyclic" group, as the term is used herein, comprises one or more closed chains or rings, which consist entirely of carbon atoms, and which may be substituted. Included in such groups are alicyclic groups (such as cyclopropyl, cyclobutyl, cyclopentyl, cyclohexyl and adamantyl), groups containing both alkyl and cycloalkyl moieties (such as adamantanemethyl), and aromatic groups (such as phenyl, naphthyl, indanyl, fluorenyl, (1,2,3,4)-tetrahydronaphthyl, indenyl and isoindenyl).

The term "aryl" is used herein to refer to aromatic carbocyclic groups, including those mentioned above, which may be substituted.

A "heterocyclic" group comprises one or more closed chains or rings which have at least one atom other than carbon in the closed chain or ring, and which may be substituted. Examples include benzimidazolyl, thienyl, furanyl, pyrrolyl, imidazolyl, pyrazolyl, thiazolyl, isothiazolyl, oxazolyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, piperazinyl, morpholinyl, thionaphthyl, benzofuranyl, isobenzofuryl, indolyl, oxyindolyl, isoindolyl, indazolyl, indolinyl, 7-azaindolyl, isoindazolyl, benzopyranyl, coumarinyl, isocoumarinyl, quinolyl, isoquinolyl, naphthridinyl, cinnolinyl, quinazolinyl, pyridopyridyl, benzoxazinyl, quinoxadinyl, chromenyl, chromanyl, isochromanyl and carbolinyl.

When reference is made herein to a substituted carbocyclic group (such as substituted phenyl) or a substituted heterocyclic group, the substituents are preferably from 1 to 3 in number and selected from C$_1$ to C$_6$ alkyl, C$_1$ to C$_6$ alkoxy, C$_1$ to C$_6$ alkylthio, carboxy, carboxy(C$_1$ to C$_6$)alkyl, formyl, C$_1$ to C$_6$ alkylcarbonyl, C$_1$ to C$_6$ alkylcarbonylalkoxy, nitro, trihalomethyl, hydroxy, amino, C$_1$ to C$_6$ alkylamino, di(C$_1$ to C$_6$ alkyl)amino, halo, sulfamoyl and cyano.

The term "halogen", as used herein, refers to any of fluorine, chlorine, bromine and iodine.

We have found that a number of compounds in the prior art have shown a significant discrepancy in their activity as measured by two ileum based assays which are described below. We would interpret discrepancies between the functional and binding assays of greater than about 0.5 log units as significant. Analysis of data obtained in these particular functional and radioligand binding assays and also in other related bioassays suggests that the discrepancy may be connected, at least in part, with residual efficacy inherent in these structures. In practice, this means that these particular compounds may act as agonists, at least in some tissues.

Surprisingly, we have found that the compounds disclosed herein do not show a significant discrepancy in the two assays. Thus, these compounds may be considered to have minimal potential to express agonist action, and would be expected to behave as antagonists or, at constitutively-active receptors, as inverse agonists. In one aspect, therefore, the present invention provides the use of these compounds as histamine antagonists or inverse agonists, and in the manufacture of medicaments for this purpose.

Pharmaceutically acceptable salts of the acidic or basic compounds of the invention can of course be made by conventional procedures, such as by reacting the free base or acid with at least a stoichiometric amount of the desired salt-forming acid or base.

It is anticipated that the compounds of the invention can be administered by oral or parenteral routes, including intravenous, intramuscular, intraperitoneal, subcutaneous, rectal and topical administration, and inhalation.

For oral administration, the compounds of the invention will generally be provided in the form of tablets or capsules or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

Effective doses of the compounds of the present invention may be ascertained by conventional methods. The specific dosage level required for any particular patient will depend on a number of factors, including the severity of the condition being treated, the route of administration and the weight of the patient. In general, however, it is anticipated that the daily dose (whether administered as a single dose or as divided doses) will be in the range 0.001 to 5000 mg per day, more usually from 1 to 1000 mg per day, and most usually from 10 to 200 mg per day. Expressed as dosage per unit body weight, a typical dose will be expected to be between 0.01 µg/kg and 50 mg/kg, especially between 10 µg/kg and 10 mg/kg, e.g. between 100 µg/kg and 2 mg/kg.

Compounds according to Formula I in which X is —NH— can conveniently be prepared via the key intermediates 2a and 2b (FIG. 1), using the existing methods of Tozer[5] and Thompson[6]. In FIG. 1, Z is H or a Boc group or other suitable migrating group, $Z^1$ is a protecting group, $Z^2$ is H or a further protecting group, and $R^{2a}$ is $C_1$ to $C_{18}$ hydrocarbylene. Compound 2b may also be obtained from compound 2a when Z is other than H by treatment with a base such as caesium carbonate. Compound 2a may be deprotected e.g. with trifluoroacetic acid to yield a compound of the formula

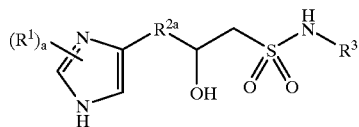

If compound 2b is deprotected under appropriate conditions, the result is a compound of the formula (II)

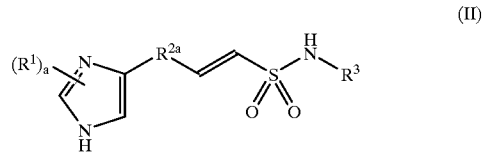

If compound 2b is reduced (e.g. by hydrogenation over a palladium/charcoal catalyst), and then deprotected, the result is a compound of formula

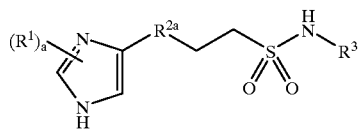

If compound 2b is allowed to react with an amine $R^8R^9NH$ and deprotected, then a compound of the formula

Figure 2:
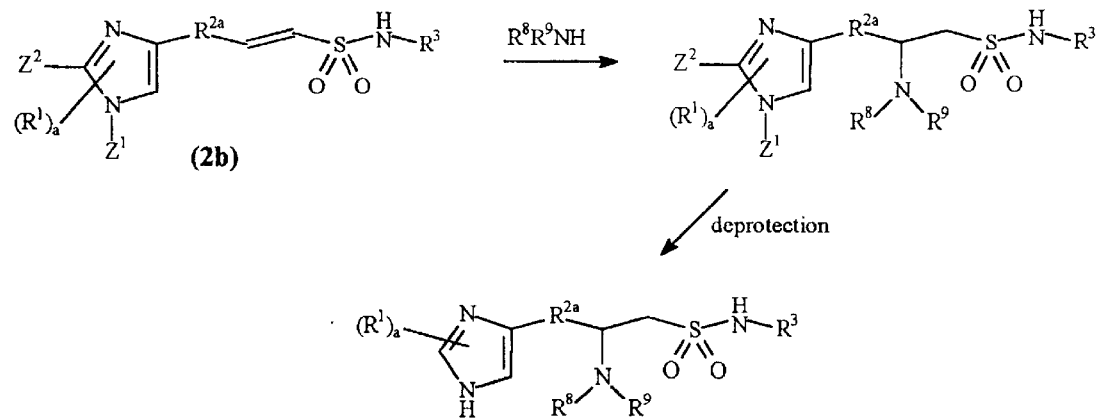

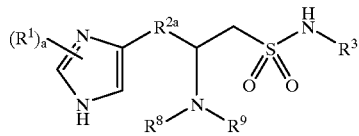

is produced. This route is shown in FIG. 2. $R^8$ and $R^9$ are independently H, lower (eg $C_1$ to $C_5$) alkyl, or are linked to each other to form an N-containing ring.

Compound (1) in FIG. 1 may be prepared by conventional methods, such as by reaction of mesyl chloride with a compound of formula $R^3NH_2$ in the presence of a base such as triethylamine. If Z is other than H, the methanesulfonamide $R^3NHSO_2Me$ may be treated with suitable reagents for protection (e.g. $Boc_2O$, catalytic DMAP) to give compound (1).

Compounds of Formula I in which X is —NH— may also be prepared by reacting a compound of formula

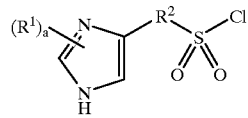

with a compound of formula $R^3NH_2$ in the presence of a base.

When X is —$NR^4$— and $R^4$ is other than H, the $R^4$ group may be introduced by chemistry on late-stage protected intermediates well known to those skilled in the art.

Compounds of Formula I in which X represents a bond may be obtained by reacting a suitably protected compound of formula

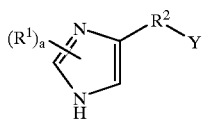

(wherein Y represents a leaving group such as bromide) with a compound of formula R³SH, followed by oxidation of the resulting thioether to yield the desired sulfone. Protection of the imidazole ring may conveniently be by means of the procedure described in Example 23 below. Oxidation of the thioether can be achieved using a suitable oxidising agent such as Oxone®.

Figure 3:
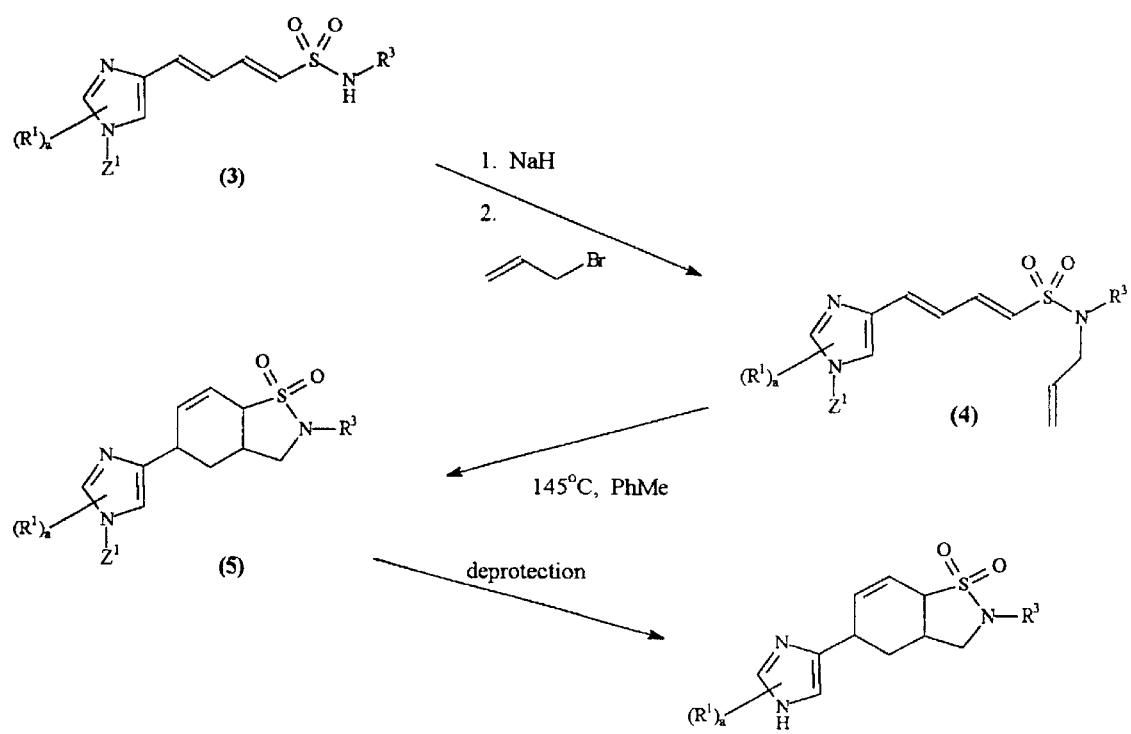

Compounds of Formula I in which X represents —NR⁴— and R⁴ represents a bond to R² may be prepared by methods analogous to that illustrated in FIG. 3. Compound (3) in FIG. 3 is a suitably N-protected derivative of the compound of Formula II above in which $R^{2a}$ is —CH=CH—. This compound is treated with sodium hydride, and then with allyl bromide, to form the N-allyl derivative (4). Ring closure is then effected by heating under pressure in a suitable dry solvent such as toluene.

The invention is now further illustrated by means of the following examples. All reactions were performed under an atmosphere of dried argon unless otherwise stated. Dichloromethane (DCM) was freshly distilled from calcium hydride. Tetrahydrofuran (THF) was freshly distilled from sodium-benzophenone ketyl.

EXAMPLE 1

N-(4-Chlorobenzyl)-4-(1H-imidazol-4-yl)-1-butanesulfonamide

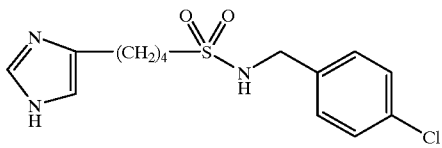

Step a. N-(4-chlorobenzyl)-methanesulfonamide. A solution of 4-chlorobenzylamine (12.20 g, 86.2 mmol) and triethylamine (14.4 ml, 103 mmol) in DCM (200 ml) was cooled in an ice bath. Mesyl chloride (7.34 ml, 94.9 mmol) was added dropwise and the solution was stirred for 10 min. The cold bath was removed and the solution stirred for a further 2 h. The reaction was diluted with an equal volume of DCM and washed with 10% citric acid solution and brine. The solvent was evaporated and the residue recrystallised from hot ethyl acetate. The product was thus obtained as a colourless crystalline solid (15.3 g, 81%).

Step b. N-(tert-butoxycarbonyl)-N-(4-chlorobenzyl)-methanesulfonamide. To a solution of the product from step a (15.30 g, 69.6 mmol) and di-tert-butyl-dicarbonate (18.27 g, 83.6 mmol) in DCM (150 ml) was carefully added N,N-dimethylaminopyridine (848 mg, 6.96 mmol); there was immediate and vigorous effervescence. The solution was stirred for 30 min, by which time effervescence had ceased. The solution was diluted to a total volume of 500 ml with DCM and washed twice with 10% citric acid solution and then brine. The solvent was evaporated to give yellow solid which was recrystallised from hot propan-2-ol (100 ml). The precipitate was collected by filtration and dried in vacuo at 50° C. to afford the product as a colourless crystalline solid (19.70 g, 89%).

Step c. 3-[1-(triphenylmethyl)imidazol-4-yl]propanal. A solution of oxalyl chloride (1.75 ml, 20.1 mmol) in DCM (60 ml) was cooled to −78° C. and dimethylsulfoxide (2.85 ml, 20.1 mmol) was added dropwise, with concomitant effervescence. The solution was stirred for 5 min, by which time effervescence had ceased, and a solution of 3-[1-(triphenylmethyl)imidazol-4-yl]propan-1-ol (6.17 g, 16.7 mmol)[1] in DCM (30 ml) was added by means of a cannula. The solution was stirred for 20 min, triethylamine (8.40 ml, 60.2 mmol) was added, the cold bath was removed and the resultant solution stirred for 3 h. A column of silica was flushed with an equal volume of ethyl acetate. The reaction mixture was applied to the top of the column and the column eluted to dryness. This was repeated with a column's volume of DCM to ensure complete removal of dimethylsulfide. The column was eluted with ethyl acetate and the aldehyde collected in fractions. The combined fractions were evaporated to give the product as a white solid (4.94 g, 81%).

Step d. tert-butyl (1-((((4-chlorobenzyl)amino)sulfonyl)methyl)-3-(1-(triphenylmethyl) imidazol-4-yl)propyl) carbonate. A solution of N-(tert-butoxycarbonyl)-N-(4-chlorobenzyl)-methanesulfonamide (step b) (204 mg, 0.64 mmol) in THF (2.5 ml) was cooled to −78° C., 1.5M lithium diisopropylamide (430 μl, 0.64 mmol) was added dropwise and the solution was stirred for 30 min. A solution of the aldehyde from step c of this example (194 mg, 0.53 mmol) was added by means of a cannula, the cold bath was removed and the solution was stirred for 2 h. The reaction mixture was quenched with saturated ammonium chloride solution (10 ml) and extracted with diethyl ether (2×10 ml). The combined extracts were washed with brine, dried over sodium sulfate, filtered and the solvent evaporated. Flash column chromatography (silica, ethyl acetate) of the residue gave the product ($R_f$ 0.5) as a colourless foam (146 mg, 40%): ¹H NMR (300 MHz, CDCl₃) 7.33(10H, m), 7.25(4H, m), 7.10(6H, m), 6.55(1H, s), 6.13(1H, t), 5.15(1H, m), 4.25(2H, d), 3.40(1H, dd), 3.16(1H, dd), 2.62(2H, m), 2.18(2H, m), 1.96(2H, m), 1.45(9H, s).

Step e. (E)-N-(4-chlorobenzyl)-4-(1-(triphenylmethyl) imidazol-4-yl)-1-but-1-enesulfonamide. To a solution of the product from the previous step (146 mg, 0.21 mmol) in anhydrous methanol (3 ml) was added cesium carbonate (140 mg, 0.42 mmol). The mixture was stirred overnight and the solvent evaporated. The residue was purified by flash column chromatography (silica, ethyl acetate) and gave the product ($R_f$ 0.3) as a colourless foam (85 mg, 72%): ¹H NMR (300 MHz, CDCl₃) 7.33(10H, m), 7.30(2H, d), 7.21 (2H, d), 7.12(6H, m), 6.77(1H, dt, J=15, 7 Hz), 6.55(1H, d), 6.15(1H, J=15, 1.5 Hz), 4.61(1H, t), 4.14(2H, d), 2.67(2H, m), 2.58(2H, m).

Step f. (E)-N-(4-chlorobenzyl)-4-(1-(triphenylmethyl) imidazol-4-yl)-1-butanesulfonamide. A round bottom flask containing the product from the previous step (282 mg, 0.50 mmol), 10% palladium-on-charcoal (34 mg) and THF (10 ml) was evacuated and flushed with hydrogen three times. The mixture was vigorously stirred overnight under an atmosphere of hydrogen. The catalyst was removed by filtration and the filtrate evaporated. The residue was purified by flash column chromatography (silica, ethyl acetate) and gave the product ($R_f$ 0.3) as a colourless foam (190 mg, 67%): ¹H NMR (300 MHz, CDCl₃) 7.32(10H, m), 7.27(4H, m), 7.12(6H, m), 6.53(1H, d), 5.45(1H, t), 4.23(2H, d), 2.97(2H, t), 2.53(2H, t), 1.79(4H, m).

Step g. Trifluoroacetic acid (3 ml) was added to the product from the previous step (190 mg, 0.33 mmol). The flask was stoppered and the resultant yellow solution left to stand overnight under ambient conditions. The solvent was evaporated and the residue purified by flash column chromatography (silica, 1:10:90 ammonia(880)/methanol/dichloromethane). Thus, the title compound ($R_f$ 0.3) was isolated as a colourless oil (76 mg, 70%): $^1$H NMR (300 MHz, $d_4$-MeOH) 7.57(1H, s), 7.34(4H, s), 6.79(1H, d), 4.19(2H, s), 2.97(2H, t), 2.58(2H, t), 1.72(4H, m). The maleate salt was prepared by lyophilisation of an equimolar solution of the product and maleic acid in water/dioxan. Found: C, 48.95; H, 5.00; N, 9.47%; $C_{18}H_{22}ClN_3O_6S$ requires: C, 48.70; H, 5.00; N, 9.47%.

EXAMPLE 2

N-(4-Chlorobenzyl)-2-hydroxy-4-(1H-imidazol-4-yl)-1-butanesulfonamide

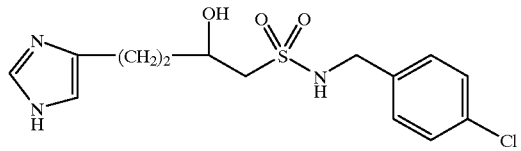

tert-Butyl (1-((((4-chlorobenzyl)amino)sulfonyl)methyl)-3-(1-(triphenylmethyl)imidazol-4-yl)propyl) carbonate (Example 1, step d) (137 mg, 0.20 mmol) was deprotected and purified according to the procedure of Example 1, step g and the title compound ($R_f$ 0.15, 1:10:90 ammonia(880)/methanol/dichloromethane) was isolated as a white solid (56 mg, 70%): $^1$H NMR (300 MHz, $d_4$-MeOH) 7.57(1H, d), 7.34(4H, s), 6.81(1H, d), 4.22(2H, s), 4.08(1H, m), 3.15(2H, m), 2.70(2H, m), 1.85(2H, m). The maleate salt was prepared by lyophilisation of an equimolar solution of the product and maleic acid in water/dioxan. Found: C, 46.85; H, 5.06; N, 8.86%; $C_{18}H_{22}ClN_3O_7S$ requires: C, 47.01; H, 4.82; N, 9.14%.

EXAMPLE 3

(E)-N-(4-Chlorobenzyl)-4-(1H-imidazol-4-yl)-1-but-1-enesulfonamide

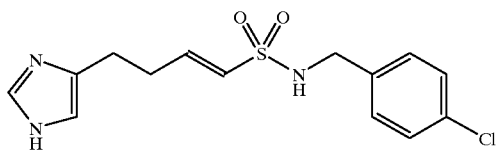

(E)-N-(4-Chlorobenzyl)4-(1-(triphenylmethyl)imidazol-4-yl)-1-but-1-enesulfonamide (Example 1, step e) (85 mg, 0.15 mmol) was deprotected and purified according to the procedure of Example 1, step g and the title compound ($R_f$ 0.25, 1:10:90 ammonia(880)/methanol/dichloromethane) was isolated as a white solid (39 mg, 80%): $^1$H NMR (300 MHz, $d_4$-MeOH) 7.60(1H, d), 7.31(4H, m), 6.84(1H, d), 6.65(1H, dt, J=15, 7 Hz), 6.23(1H, dt, J=15, 1.5 Hz), 3.99(2H, s), 2.74(2H, t), 2.57(2H, dd).The maleate salt was prepared by lyophilisation of an equimolar solution of the product and maleic acid in water/dioxan. Found: C, 48.64; H, 4.74; N, 9.46%; $C_{18}H_{20}ClN_3O_6S$ requires: C, 48.93; H, 4.56; N 9.51%.

EXAMPLE 4

N-(4-Chlorobenzyl)-2-oxy-4-(1H-imidazol-4-yl)-1-butanesulfonamide

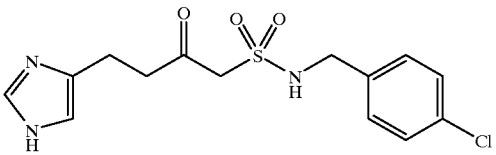

Step a. N-(4-chlorobenzyl)-2-hydroxy-4-(1-(triphenylmethyl)imidazol-4-yl)-1-butanesulfonamide. A solution of N-(4-chlorobenzyl)-methanesulfonamide (Example 1, step a) (314 mg, 1.43 mmol) in THF (4.5 ml) was cooled to −78° C., 1.5M lithium diisopropylamide (1.95 ml, 2.93 mmol) was added dropwise and the solution was stirred for 30 min. A solution of 3-[1-(triphenylmethyl)imidazol-4-yl]propanal (Example 1, step c) (314 mg, 1.30 mmol) was added by means of cannula, the cold bath was removed and the solution was stirred overnight. The reaction mixture was quenched with saturated ammonium chloride solution (20 ml) and extracted with diethyl ether (2×20 ml). The combined extracts were washed with brine, dried over sodium sulfate, filtered and the solvent evaporated. Flash column chromatography (silica, ethyl acetate) of the residue gave the product ($R_f$ 0.2) as a colourless oil (313 mg, 37%): $^1$H NMR (300 MHz, CDCl$_3$) 7.34(10H, m), 7.29(4H, m), 7.13(6H, m), 6.58(1H, s), 5.42(1H, t), 4.34(1H, m), 4.26(2H, m), 3.22(1H, dd), 3.07(1H, dd), 2.75(2H, m), 1.84(2H, m).

Step b. N-(4-chlorobenzyl)-2-oxy-4-(1-(triphenylmethyl)imidazol-4-yl)-1-butanesulfonamide. The hydroxy compound produced in the previous step was oxidised and purified using the procedure of Example 1, step c. The ketone product ($R_f$ 0.4, ethyl acetate) was thereby isolated as a colourless oil (195 mg, 68%): $^1$H NMR (300 MHz, CDCl$_3$) 8.10(1H, t), 7.33(10H, m), 7.21(2H, d), 7.15(2H, d), 7.04 (6H, m), 6.52(1H, s), 4.22(2H, d), 4.21(2H, s), 3.12(2H, t), 2.91(2H, t).

Step c. The product from the previous step (190 mg, 0.33 mmol) was deprotected and purified according to the procedure of Example 1, step g and the title compound ($R_f$ 0.20, 1:10:90 ammonia(880)/methanol/dichloromethane) was isolated as a white solid (90 mg, 80%). The maleate salt was prepared by lyophilisation of an equimolar solution of the product and maleic acid in water/dioxan: $^1$H NMR (300 MHz, $d_6$-DMSO) 8.77(1H, s), 8.00(1H, t), 7.40(2H, d), 7.34(2H, d), 7.28(1H, s), 6.03(2H, s), 4.30(2H, s), 4.15(2H, d), 3.04(2H, t), 2.82(2H, t). Found: C, 46.47; H, 4.64; N, 9.05%; $C_{18}H_{20}ClN_3O_7S.0.45H_2O$ requires: C, 46.39; H, 4.52; N, 9.02%.

EXAMPLE 5

N-(4-Chlorobenzyl)-5-(1H-imidazol-4-yl)-1-pentanesulfonamide

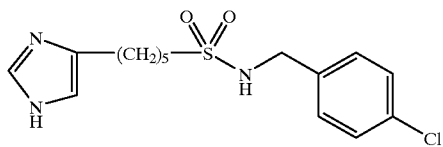

Step a. (Z)-4-[4-(1,3-dioxolan-2-yl)but-2-enyl]-1-(triphenylmethyl)-imidazole. A suspension of [2-(1,3- dioxolan-2-yl)ethyl]triphenylphosphonium bromide (48.5 g, 109 mmol) in tetrahydrofuran (500 ml) was cooled to −20° C. 1.6M n-Butyl lithium (68.3 ml, 109 mmol) was added dropwise and the solution stirred for 1 h. A solution of [1-(triphenylmethyl)imidazol-4-yl]carbaldehyde[2] (36.8 g, 109 mmol) in tetrahydrofuran (500ml) was added slowly and the reaction mixture stirred at room temperature for 18 h. The reaction mixture was concentrated in vacuo, water was added and the mixture filtered through a pad of Celite. The filtrate was extracted with dichloromethane (2×500 ml) and the combined extracts dried over magnesium sulfate. Filtration and evaporation gave a yellow oil. From flash column chromatography (silica; 10–20% ethyl acetate/hexane) the product was isolated as a yellow oil (19.7 g, 42%).

Step b. 4-[4-(1,3-dioxolan-2-yl)butyl]-1-(triphenylmethyl)-imidazole. A solution of the product from step a in ethanol was hydrogenated in the presence of a catalytic quantity of 10% palladium-on-charcoal at atmospheric pressure and temperature for 18 h. The product was isolated as a colourless oil in quantitative yield.

Step c. 4-[1-(triphenylmethyl)imidazol-4-yl]butanal. A suspension of the product from step b (19.8 g, 46.6 mmol) in a mixture of acetone (300 ml) and 2M hydrochloric acid (50 ml) was stirred at room temperature for 20 h. The mixture was neutralised with sodium hydrogen carbonate, filtered and the filtrate extracted with dichloromethane (3×100 ml). The combined extracts were dried over magnesium sulfate, filtered and evaporated to give the product as a colourless oil (16.1 g, 91%).

Step d. tert-butyl (1-((((4-chlorobenzyl)amino)sulfonyl)methyl)-4-(1-(triphenylmethyl)imidazol-4-yl)butyl) carbonate. A solution of N-(tert-butoxycarbonyl)-N-(4-chlorobenzyl)-methanesulfonamide (Example 1, step b) (1.53 g, 4.80 mmol) in THF (16 ml) was cooled to −78° C., 1.5M lithium diisopropylamide (3.20 ml, 4.80 mmol) was added dropwise and the solution was stirred for 1 h. A solution of the aldehyde from step c of this example (1.83 g, 4.80 mmol) in THF(16 ml) was added by means of a cannula, the cold bath was removed and the solution was stirred for 2 h. The reaction was quenched with saturated ammonium chloride solution (20 ml) and the mixture was extracted with ethyl acetate (2×20 ml). The combined extracts were washed with brine, dried over sodium sulfate, filtered and the solvent evaporated. Flash column chromatography (silica, 50% ethyl acetate/toluene) of the residue gave the product ($R_f$ 0.4) as a colourless oil (1.60 g, 48%): $^1$H NMR (300 MHz, CDCl$_3$) 7.33(10H, m), 7.22(4H, m), 7.10(6H, m), 6.52(1H, d), 6.47(1H, t), 5.11(1H, m), 4.26(2H, d), 3.38(1H, dd), 3.11(1H, dd), 2.55(2H, t), 1.87(1H, m), 1.68(3H, m), 1.47(9H, s).

Step e. (E)-N-(4-chlorobenzyl)-5-(1-(triphenylmethyl)imidazol-4-yl)-1-pent-1-enesulfonamide. The elimination reaction on the product from the previous step (1.60 g, 2.29 mmol) was performed according to the procedure of Example 1, step e. The vinylsulfonamide product ($R_f$ 0.5, ethyl acetate) was thus obtained as a white solid (1.20 g, 91%): $^1$H NMR (300 MHz, CDCl$_3$) 7.33(10H, m), 7.26(4H, m), 7.14(6H, m), 6.77(1H, dt, J=15,7 Hz), 6.53(1H, d), 6.11(1H, d, J=15 Hz), 4.66(1H, t), 4.14(2H, d), 2.56(2H, d), 2.23(2H, dd), 1.79(2H, quint.).

Step f. N-(4-chlorobenzyl)-5-(1-(triphenylmethyl)imidazol-4-yl)-1-penlanesulfonamide. The hydrogenation of the product from the previous step was performed according to the procedure of Example 1, step f. The product ($R_f$ 0.5, 0.5:5:95 ammonia(880)/methanol/dichloromethane) was thus obtained as a colourless oil: $^1$H NMR (300 MHz, CDCl$_3$) 7.33(10H, m), 7.28(4H, m), 7.12(6H, m), 6.52(1H, d), 5.45(1H, m), 4.24(2H, d), 2.96(2H, t), 2.53(2H, t), 1.81(2H, m), 1.63(2H, m), 1.46(2H, m).

Step g. The product from the previous step (148 mg, 0.25 mmol) was deprotected and purified according to the procedure of Example 1, step g and the title compound ($R_f$ 0.30, 1:10:90 ammonia(880)/methanol/dichloromethane) was isolated as a white solid (73 mg, 84%): $^1$H NMR (300 MHz, d$_4$-MeOH) 7.59(1H, d), 7.35(4H, m), 6.78(1H, s), 4.20(2H, s), 2.93(2H, t), 2.58(2H, t), 1.74(2H, quin.), 1.62(2H, quin.), 1.39(2H, quin.). The maleate salt was prepared by lyophilisation of an equimolar solution of the product and maleic acid in water/dioxan. Found: C, 49.70; H, 5.24; N, 9.18%; $C_{19}H_{24}ClN_3O_6S$ requires: C, 49.83; H, 5.28; N, 9.18%.

EXAMPLE 6

N-(4-Chlorobenzyl)-2-hydroxy-5-(1H-imidazol-4-yl)-1-pentanesulfonamide

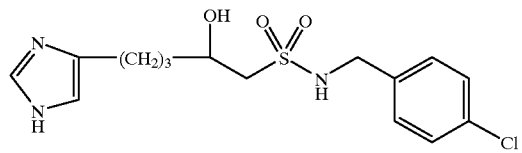

tert-Butyl (1-((((4-chlorobenzyl)amino)sulfonyl)methyl)-4-(1-(triphenylmethyl)imidazol-4-yl)butyl) carbonate (Example 5, step d) was deprotected and purified according to the procedure of Example 1, step g and the title compound ($R_f$ 0.3, 1:10:90 ammonia(880)/methanol/dichloromethane) was isolated as a colourless oil: $^1$H NMR (300 MHz, d$_4$-MeOH) 7.56(1H, d), 7.35(4H, m), 6,78(1H, d), 4.22(2H, s), 4.08(1H, m), 3.10(2H, m), 2.60(2H, m), 1.75(2H, m), 1.53(2H, m). The maleate salt was prepared by lyophilisation of an equimolar solution of the product and maleic acid in water/dioxan. Found: C, 47.78; H, 5.27; N, 8.61%; $C_{19}H_{24}ClN_3O_7S$ requires: C, 48.15; H, 5.10; N, 8.87%.

EXAMPLE 7

N-(4-Chlorobenzyl)-6-(1H-imidazol-4-yl)-1-hexanesulfonamide

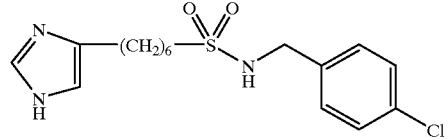

Step a. (E)-5-[1-(triphenylmethyl)-4-imidazolyl]-pent-2-enoate. A suspension of sodium hydride (60% dispersion in oil) (1.43 g, 36.0 mmol) in THF (20 ml) was cooled in an ice-bath and a solution of triethylphosphonoacetate (7.20 ml, 35.6 mmol) in THF (50 ml) was added over 10 min. The mixture was allowed to warm to room temperature, stirred for 20 min and cooled to −20° C. A solution of 3-[1-(triphenylmethyl)imidazol-4-yl]propun-1-al (Example 1, step c) (10.60 g, 28.9 mmol) in THF (100 ml) was added over 30 min, the mixture allowed to warm to room temperature and stirring continued for 1.5 h. The reaction mixture was diluted with ethyl acetate (150 ml), washed 10% citric acid solution (2×150 ml) and brine (2×150 ml), and dried over sodium sulfate. Filtration and evaporation of the filtrate gave the product as a yellow oil in quantitative yield.

Step b. 5-[1-(triphenylmethyl)-4-imidazolyl]-pentanoate. A round bottom flask containing the product from the previous step (12.6 g, 29.0 mmol), 10% palladium-on-charcoal (1.03 g) and 1:10 methanol/THF (220 ml) was evacuated and flushed with hydrogen three times. The mixture was vigorously stirred overnight under an atmosphere of hydrogen. The catalyst was removed by filtration and the filtrate evaporated. The residue was purified by flash column chromatography (silica, 30–60% ethyl acetate/DCM) and gave the product as a white solid (6.34 g, 50%).

Step c. 5-[1-(triphenylmethyl)imidazol-4-yl]pentan-1-ol. A suspension of lithium aluminium hydride (346 mg, 9.1 mmol) in THF (100 ml) was cooled in an ice-bath and a solution of the product from the previous step (6.34 g, 14.5 mmol) in THF (50 ml) was added over 30 min. The mixture was stirred at room temperature for 2 h and then at reflux for 3 h. The mixture was allowed to cool to room temperature, 1.0M lithium aluminium hydride in diethyl ether (8 ml, 8.0 mmol) was added over 5 min, and stirring continued for 18 h. 50% Ethyl acetate/THF (60 ml) was added dropwise followed by sodium sulfate decahydrate (10 g). The resultant precipitate was removed by filtration and the filtrate evaporated to give a yellow oil, which solidified on standing. The solid was triturated with diethyl ether and collected by filtration (3.75 g, 65%).

Step d. 5-[1-(triphenylmethyl)imidazol-4-yl]pentanal. The hydroxy compound (1.60 g, 4.04 mmol) produced in the previous step was oxidised and purified using the procedure of Example 1, step c. The product ($R_f$ 0.2, ethyl acetate) was thus obtained as a yellow oil (1.08 g, 68%).

Step e. tert-butyl (1-((((4-chlorobenzyl)amino)sulfonyl) methyl)-5-(1-(triphenylmethyl) imidazol-4-yl)pentyl) carbonate. 5-[1-(Triphenylmethyl)imidazol-4-yl]pentanal (1.05 g, 2.66 mmol), from the previous step and N-(tert-butoxycarbonyl)-N-(4-chlorobenzyl)-methanesulfonamide (934 mg, 2.92 mmol) (Example 1, step b) were reacted together according to the procedure of Example 5, step d. The product ($R_f$ 0.3, 50% ethyl acetate/toluene) was thus obtained as a colourless oil (722 mg, 38%).

Step f. N-(4-chlorobenzyl)-6-(1-(triphenylmethyl) imidazol-4-yl)-1-hex-1-enesulfonamide. The elimination reaction on the product from the previous step (710 mg, 0.99 mmol) was performed according to the procedure of Example 1, step e. The vinylsulfonamide product ($R_f$ 0.5, 50% ethyl acetate/toluene) was thus obtained as a colourless oil (452 mg, 77%).

Step g. N-(4-chlorobenzyl)-6-(1-(triphenylmethyl) imidazol-4-yl)-1-hexane sulfonamide. The hydrogenation of the product from the previous step (452 mg, 0.76 mmol) was performed according to the procedure of Example 1, step f. The product was thus obtained as a colourless oil (423 mg, 93%).

Step h. The product from the previous step (420 mg, 070 mmol) was deprotected and purified according to the procedure of Example 1, step g and the title compound ($R_f$ 0.35, 1:10:90 ammonia(880)/methanol/dichloromethane) was isolated as a white solid (183 mg, 77%): $^1$H NMR (300 MHz, d4-MeOH) 7.56(1H, d), 7.35(4H, m), 6.76(1H, s), 4.20(2H, s), 2.92(2H, m), 2.58(2H, t), 1.72(2H, m), 1.62(2H, m), 1.35(4H, m). The maleate salt was prepared by lyophilisation of an equimolar solution of the product and maleic acid in water/dioxan. Found: C, 50.67; H, 5.63; N, 9.01%, $C_{20}H_{26}ClN_3O_6S$ requires: C, 50.90; H, 5.55; N, 8.90%.

EXAMPLE 8

N-(4-Chlorobenzyl)-2-hydroxy-6-(1H-imidazol-4-yl)-1-hexanesulfonamide

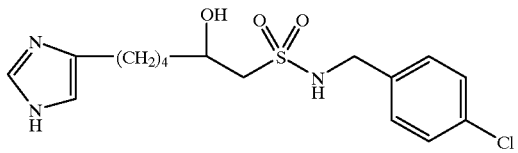

tert-Butyl (1-((((4-chlorobenzyl)amino)sulfonyl)methyl)-5-(1-(triphenylmethyl)imidazol-4-yl)pentyl) carbonate (194 mg, 0.28 mmol) (Example 7, step e) was deprotected and purified according to the procedure of Example 1, step g and the title compound ($R_f$ 0.2, 1:10:90 ammonia(880)/methanol/dichloromethane) was isolated as a colourless oil (80 mg, 77%): $^1$H NMR (300 MHz, $d_4$-MeOH) 7.56(1H, s), 7.35(4H, m), 6.77(1H, s), 4.22(2H, s), 4.04(1H, m), 3.08 (2H, m), 2.60(2H, m), 1.66(2H, m), 1.53(2H, m), 1.37(2H, m). The maleate salt was prepared by lyophilisation of an equimolar solution of the product and maleic acid in water/dioxan. Found: C, 47.52; H, 5.44; N, 8.36%; $C_{20}H_{26}ClN_3O_7S$ requires: C, 47.65; H, 5.56; N, 8.33%.

EXAMPLE 9

N-(4-Chlorophenethyl)-4-(1H-imidazol-4-yl)-1-butanesulfonamide

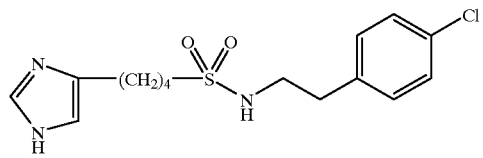

N-(tert-Butoxycarbonyl)-N-(4-chlorophenethyl)-methanesulfonamide was prepared from 4-chlorophenethylamine according to the procedure of Example 1, steps a and b. It was reacted with 3-[1-(triphenylmethyl)imidazol-4-yl]propan-1-al (Example 1, step c) according to the procedure of Example 5, step d to produce tert-butyl (1-((((4-chlorophenethyl)amino)sulfonyl) methyl)-3-(1-(triphenyl methyl)imidazol-4-yl)propyl) carbonate. This was converted to the title compound using the procedure of Example 1, steps e to g. Thus, the title compound ($R_f$ 0.35) was isolated as a colourless oil. The maleate salt was prepared by lyophilisation of an equimolar solution of the product and maleic acid in water/dioxan. $^1$H NMR (300 MHz, $d_6$-DMSO) 8.86(1H, s), 7.34(3H, m), 7.26(2H, m), 7.11(1H, t), 6.03(2H, s), 3.13(2H, dd), 2.94 (2H, t), 2.73(2H, t), 2.62(2H, t), 1.61(4H, m). Found: C, 49.66; H, 5.33; N, 9.19%; $C_{19}H_{24}ClN_3O_6S$ requires: C, 49.83; H, 5.28; N, 9.18%.

EXAMPLE 10

N-(4Chlorophenethyl)-2-hydroxy-4-(1H-imidazol-4-yl)-1-butanesulfonamide

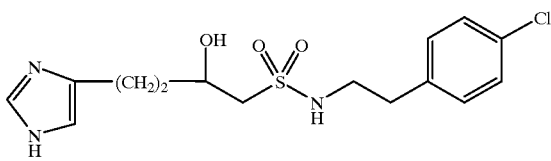

tert-Butyl (1-((((4-chlorophenethyl)amnino)sulfonyl)methyl)-3-(1-(triphenylmethyl)imidazol-4-yl)propyl) carbonate (Example 9) was deprotected and purified according to the procedure of Example 1, step g and the title compound ($R_f$ 0.2, 1:10.90 ammonia(880)/methanol/dichioromethane) was isolated as a white solid: $^1$H NMR (300 MHz, $d_4$-MeOH) 7.56(1H, d), 7.28(2H, dd), 7.22(2H, dd), 6.80 (1H, d), 4.03(1H, m), 3.26(2H, m), 3.10(2H, m), 2.82(2H, t), 2.71(2H, m), 1.88(1H, m), 1.80(1H, m). The maleate salt was prepared by lyophilisation of an equimolar solution of the product and maleic acid in water/dioxan.

EXAMPLE 11

N-(4-Chlorophenethyl)-5-(1H-imidazol-4-yl)-1-pentanesulfonamide

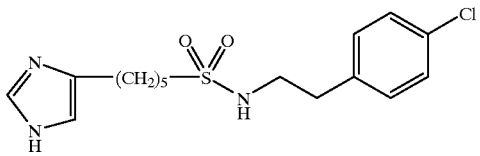

N-(tert-Butoxycarbonyl)-N-(4-chlorophenethyl)-methanesulfonamide was prepared from 4-chlorophenethylamine according to the procedure of Example 1, steps a and b. It was reacted with 4-[1-(triphenylmethyl)imidazol-4-yl]butanal (Example 5, step c) according to the procedure of Example 5, step d to produce tert-butyl (1-((((4-chlorophenethyl)amino)sulfonyl)methyl)-4-(1-(triphenylmethyl)imidazol-4-yl)butyl) carbonate. This was converted to the title compound using the procedure of Example 1, steps e to g. Thus, the title compound ($R_f$ 0.3) was isolated as a colourless oil: $^1$H NMR (300 MHz, $d_4$-MeOH) 7.55(1H, s), 7.28(2H, dt), 7.23(2H, dd), 6.77(1H, s), 4.03(1H, m), 3.27(2H, t), 2.88(2H, m), 2.83(2H, m), 2.58(2H, t), 1.65(4H, m), 1.42(2H, m). The maleate salt was prepared by lyophilisation of an equimolar solution of the product and maleic acid in water/dioxan. Found: C, 50.52; H, 5.79; N, 8.66%; $C_{20}H_{26}ClN_3O_6S$ requires: C, 50.89; H, 5.55; N, 8.91%.

EXAMPLE 12

N-(4-Chlorophenethyl)-2-hydroxy-5-(1H-imidazol-4-yl)-1-pentanesulfonamide

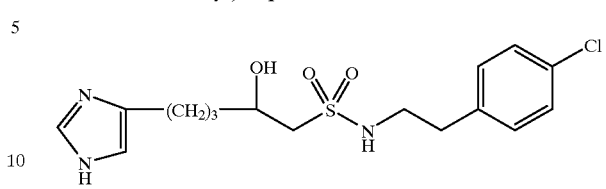

tert-Butyl (1-((((4-chlorophenethyl)amino)sulfonyl)methyl)-4-(1-(triphenylmethyl)imidazol-4-yl)butyl) carbonate (Example 11) was deprotected and purified according to the procedure of Example 1, step g and the title compound ($R_f$ 0.15, 1:10:90 ammonia(880)/methanol/dichloromethane) was isolated as a colourless oil: $^1$H NMR (300 MHz, d4-MeOH) 7.56(1H, d), 7.28(2H, dd), 7.23(2H, d), 6.78(1H, s), 4.03(1H, m), 3.28(2H, m), 3.05(2H, m), 2.82(2H, t), 2.61(2H, m), 1.75(2H, m), 1.56(2H, m). The maleate salt was prepared by lyophilisation of an equimolar solution of the product and maleic acid in water/dioxan.

EXAMPLE 13

N-Benzyl-5-(1H-imidazol-4-yl)-1-pentanesulfonamide

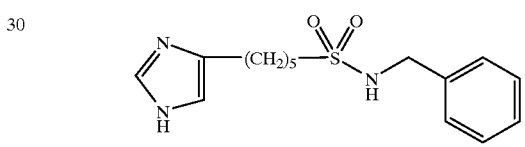

N-(tert-Butoxycarbonyl)-N-benzyl-methanesulfonamide was prepared from benzylamine essentially according to the procedure of Example 1, steps a and b. It was reacted with 4-[1-(triphenylmethyl)imidazol-4-yl]butanal (Example 5, step c) according to the procedure of Example 5, step d to produce tert-butyl (1-(((benzylamino)sulfonyl)methyl)-4-(1-(triphenylmethyl)imidazol-4-yl)butyl) carbonate. This was converted to the title compound using the procedure of Example 1, steps e to g. Thus, the title compound ($R_f$ 0.4) was isolated as a colourless oil: $^1$H NMR (300 MHz, $d_4$-MeOH) 7.55(1H, s), 7.30(5H, m), 6.75(1H, s), 4.22(2H, s), 2.86(2H, t), 2.55(2H, t), 1.68(2H, quin.), 1.56(2H, quin.), 1.34(2H, quin.). The maleate salt was prepared by lyophilisation of an equimolar solution of the product and maleic acid in water/dioxan. Found: C, 53.87; H, 6.03; N, 10.03%; $C_{19}H_{25}N_3O_6S$ requires: C, 53.89; H, 5.95; N, 9.92%.

EXAMPLE 14

N-Benzyl-2-hydroxy-5-(1H-imidazol-4-yl)-1-pentanesulfonamide

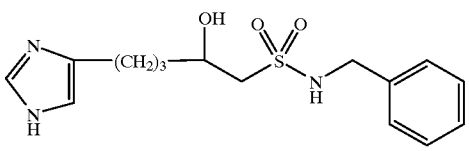

tert-Butyl (1-(((benzylamino)sulfonyl)methyl)-4-(1-(triphenylmethyl)imidazol-4-yl)butyl) carbonate (Example 13) was deprotected and purified according to the procedure of Example 1, step g and the title compound ($R_f$ 0.15, 1:10:90 ammonia(880)/methanol/dichloromethane) was isolated as a colourless oil: $^1$H NMR (300 MHz, $d_4$-MeOH) 7.57(1H, d), 7.30(5H, m), 6.78(1H, s), 4.24(2H, m), 4.03 (1H, m), 3.04(2H, m), 2.59(2H, m), 1.71(2H, m), 1.52(2H, m). The maleate salt was prepared by lyophilisation of an equimolar solution of the product and maleic acid in water/dioxan.

EXAMPLE 15

N-(4-Bromobenzyl)-5-(1H-imidazol-4-yl)-1-pentanesulfonamide

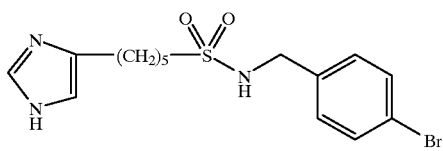

N-(tert-Butoxycarbonyl)-N-(4-bromobenzyl)-methanesulfonamide was prepared from (4-bromobenzyl) amine essentially according to the procedure of Example 1, steps a and b. It was reacted with 4-[1-(triphenylmethyl) imidazol-4-yl]butanal (Example 5, step c) according to the procedure of Example 5, step d to produce tert-butyl (1-((((4-bromobenzyl)amino)sulfonyl)methyl)-4-(1-(triphenylmethyl)imidazol-4-yl)butyl) carbonate. This was converted to the title compound using the procedure of Example 1, steps e, f and g, with the modification to step f of the palladium catalyst being replaced by rhodium-on-alumina. Thus, the title compound ($R_f$ 0.3, 1:10:90 ammonia (880)/methanol/dichloromethane) was isolated as a colourless oil: 1H NMR (300 MHz, $d_4$-MeOH) 7.55(1H, s), 7.50(2H, d), 7.31(2H, d), 6.75(1H, s), 4.19(2H, s), 2.90(2H, t), 2.58(2H, t), 1.72(2H, quin.), 1.59(2H, quin.), 1.34(2H, quin.). The maleate salt was prepared by lyophilisation of an equimolar solution of the product and maleic acid in water/dioxan. Found: C, 45.51; H, 4.85; N, 8.28%; $C_{19}H_{24}BrN_3O_6S$ requires: C, 10 45.42; H, 4.82; N, 8.36%.

EXAMPLE 16

N-(4-Bromobenzyl)-2-hydroxy-5-(1H-imidazol-4-yl)-1-pentanesulfonamide

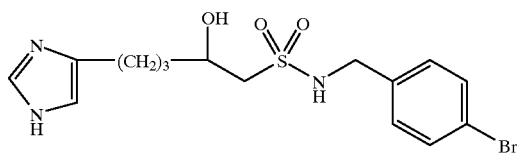

tert-Butyl (1-((((4-bromobenzyl)amino)sulfonyl)methyl)-4-(1-(triphenylmethyl)imidazol-4-yl)butyl) carbonate (Example 15) was deprotected and purified according to the procedure of Example 1, step g and the title compound ($R_f$ 0.2, 1:10:90 ammonia(880)/methanol/dichloromethane) was isolated as a colourless oil: $^1$H NMR (300 MHz, $d_4$-MeOH) 7.56(1H, s), 7.49(2H, d), 7.30(2H, d), 6.78(1H, s), 4.20(2H, m), 4.07(1H, m), 3.10(2H, m), 2.60(2H, m), 1.71(2H, m), 1.55(2H, m). The maleate salt was prepared by lyophilisation of an equimolar solution of the product and maleic acid in water/dioxan.

EXAMPLE 17

N-Cyclohexylmethyl-5-(1H-imidazol-4-yl)-1-pentanesulfonamide

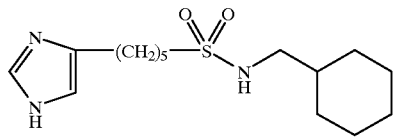

N-(tert-Butoxycarbonyl)-N-cyclohexylmethyl-methanesulfonamide was prepared from cyclohexylmethyl amine essentially according to the procedure of Example 1, steps a and b. It was reacted with 4-[1-(triphenylmethyl) imidazol-4-yl]butanal (Example 5, step c) according to the procedure of Example 5, step d to produce tert-butyl (1-(((cyclohexylmethyl amino)sulfonyl)methyl)-4-(1-(triphenylmethyl)imidazol-4-yl)butyl) carbonate. This was converted to the title compound using the procedure of Example 1, steps e to g. Thus, the title compound ($R_f$ 0.4, 1:10:90 ammonia(880)/methanol/dichloromethane) was isolated as a colourless oil: $^1$H NMR (300 MHz, $d_4$-MeOH) 7.54(1H, d), 6.77(1H, d), 3.01(2H, dd), 2.85(2H, d), 2.60 (2H, t), 1.73(9H, m), 1.57(3H, m), 1.23(3H, m), 0.93(2H, m). The maleate salt was prepared by lyophilisation of an equimolar solution of the product and maleic acid in water/dioxan. Found: C, 53.07; H, 7.40; N, 9.93%; $C_{19}H_{31}N_3O_6S$ requires: C, 53.13; H, 7.27; N, 9.78%.

EXAMPLE 18

N-Cyclohexylmethyl-2-hydroxy-5-(1H-imidazol-4-yl)-1-pentanesulfonamide tert-Butyl (1-(((cyclohexylmethylamino)sulfonyl) methyl)-4-(1-(triphenylmethyl)imidazol-4-yl)butyl) carbonate (Example 17) was deprotected and purified according to the procedure of Example 1, step g and the title compound ($R_f$ 0.15, 1:10:90 ammonia(880)/methanol/dichloromethane) was isolated as a colourless oil: $^1$H NMR (300 MHz, $d_4$-MeOH) 7.57(1H, d), 6.79(1H, s), 4.09(1H, m), 3.12(2H, d), 2.87(2H, d), 2.62(2H, t), 1.73(10H, m), 1.26(3H, m), 0.93(2H, m). The maleate salt was prepared by lyophilisation of an equimolar solution of the product and maleic acid in water/dioxan.

EXAMPLE 19

N-(2-Chlorobenzyl)-5-(1H-imidazol-4-yl)-1-pentanesulfonamide

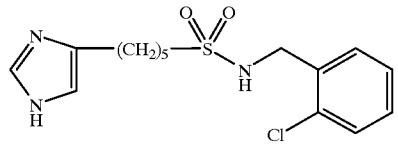

N-(tert-Butoxycarbonyl)-N-(2-chlorobenzyl)-methanesulfonamide was prepared from (2-chlorobenzyl) amine essentially according to the procedure of Example 1, steps a and b. It was reacted with 4-[1-(triphenylmethyl) imidazol-4-yl]butanal (Example 5, step c) according to the procedure of Example 5, step d to produce tert-butyl (1-((((2-chlorobenzyl)amino)sulfonyl)methyl)-4-(1-(triphenylmethyl)imidazol-4-yl)butyl) carbonate. This was converted to the title compound using essentially the procedure of Example 1, steps e to g, with the modification to step f that the palladium catalyst was replaced by rhodium-on-alumina. Thus, the title compound ($R_f$ 0.2, 1:10:90 ammonia(880)/methanol/dichloromethane) was isolated as a colourless oil: $^1$H NMR (300 MHz, $d_4$-MeOH) 7.56(1H, s), 7.50($_1$H, m), 7.39(1H, m), 7.31(2H, m), 6.75(1H, s), 4.22 (2H, s), 2.89(2H, dt), 2.56(2H, dt), 1.72(2H, m), 1.59(2H, m), 1.37(2H, m). The maleate salt was prepared by lyophilisation of an equimolar solution of the product and maleic acid in water/dioxan. Found: C, 49.59; H, 5.30; N, 8.95%; $C_{19}H_{24}ClN_3O_6S$ requires: C, 49.83; H, 5.28; N, 9.18%.

EXAMPLE 20

N-(2-Chlorobenzyl)-2-hydroxy-5-(1H-imidazol-4-yl)-1-pentanesulfonamide

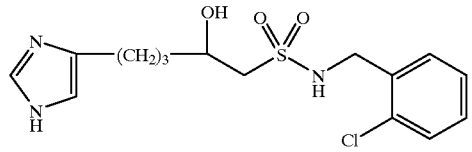

tert-Butyl (1-((((2-chlorobenzyl)amino)sulfonyl)methyl)-4-(1-(triphenylmethyl)imidazol-4-yl)butyl) carbonate (Example 19) was deprotected and purified according to the procedure of Example 1, step g and the title compound ($R_f$ 0.2, 1:10:90 ammonia(880)/methanol/dichloromethane) was isolated as a colourless oil: $^1$H NMR (300 MHz, $d_4$-MeOH) 7.57(1H, s), 7.53(1H, m), 7.39(1H, m), 7.30(2H, m), 6.78 (1H, s), 4.37(2H, s), 4.09(1H, m), 3.08(2H, m), 2.60(2H, t), 1.71(2H, m), 1.54(2H, m). The maleate salt was prepared by lyophilisation of an equimolar solution of the product and maleic acid in water/dioxan. Found: C, 49.59; H, 5.30; N, 8.95%; $C_{19}H_{24}ClN_3O_6S$ requires: C, 49.83; H, 5.28; N, 9.18%.

EXAMPLE 21

N-(3-Chlorobenzyl)-5-(1H-imidazol-4-yl)-1-pentanesulfonamide

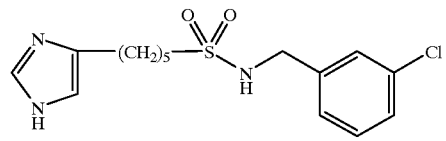

N-(tert-Butoxycarbonyl)-N-(3-chlorobenzyl)-methanesulfonamide was prepared from (3-chlorobenzyl) amine essentially according to the procedure of Example 1, steps a and b. It was reacted with 4-[1-(triphenylmethyl) imidazol-4-yl]butanal (Example 5, step c) according to the procedure of Example 5, step d to produce tert-butyl (1-((((3-chlorobenzyl)amino)sulfonyl)methyl)-4-(1-(triphenylmethyl)imidazol-4-yl)butyl) carbonate. This was converted to the title compound using the procedure of Example 1, steps e, f and g, with the modification to step f that the palladium catalyst was replaced by rhodium-on-alumina. Thus, the title compound ($R_f$ 0.3, 1:10:90 ammonia (880)/methanol/dichloromethane) was isolated as a colourless oil: $^1$H NMR (300 MHz, $d_4$-MeOH) 7.56(1H, s), 7.50(1H, m), 7.39(1H, m), 7.31(2H, m), 6.75(1H, s), 4.22 (2H, s), 2.89(2H, dt), 2.56(2H, dt), 1.72(2H, m), 1.59(2H, m), 1.37(2H, m). The maleate salt was prepared by lyophilisation of an equimolar solution of the product and maleic acid in water/dioxan. Found: C, 49.84; H, 5.26; N, 9.08%; $C_{19}H_{24}ClN_3O_6S$ requires: C, 49.83; H, 5.28; N, 9.18%.

EXAMPLE 22

N-(3-Chlorobenzyl)-2-hydroxy-5-(1H-imidazol-4-yl)-1-pentanesulfonamide

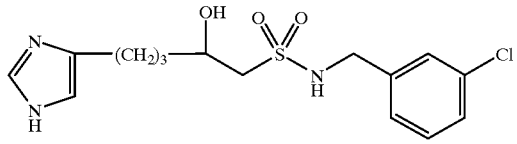

tert-Butyl (1-((((3-chlorobenzyl)amino)sulfonyl)methyl)-4-(1-(triphenylmethyl)imidazol4-yl)butyl) carbonate (Example 21) was deprotected and purified according to the procedure of Example 1, step g and the title compound ($R_f$ 0.2, 1:10:90 ammonia(880)/methanol/dichloromethane) was isolated as a colourless oil: $^1$H NMR (300 MHz, $d_4$-MeOH) 7.56(1H, s), 7.41(1H, s), 7.28(3H, m), 6.78(1H, s), 4.23(2H, s), 4.08(1H, m), 3.11(2H, m), 2.61(2H, t), 1.71(2H, m), 1.56(2H, m). The maleate salt was prepared by lyophilisation of an equimolar solution of the product and maleic acid in water/dioxan.

EXAMPLE 23

[4-(1H-Imidazol-4-yl)butyl]phenethyl sulfone

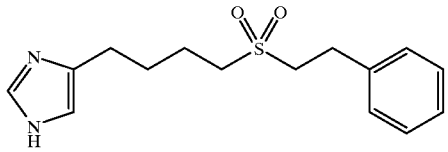

Step a. 2-(tert-butyldimethylsilyl)-1-(N,N-dimethylsulfamoyl)-imidazole. A solution of 1-(N,N-dimethylsulfamoyl)-imidazole[3] (4.48 g, 25.6 mmol) in tetrahydrofuran (100 ml) was cooled under an atmosphere of argon to −78° C. n-Butyl lithium (1.5M in hexanes) (18.0 ml, 27.0 mmol) was added over 30 min and the solution stirred for a further 30 min. To the resulting brown solution was added over 15 min a solution of tert-butyldimethylsilyl chloride (4.37 g, 28.2 mmol) in tetrahydrofuran (20 ml). The solution was allowed to warm to room temperature and stirred for 24 h. Saturated ammonium chloride solution (100 ml) and diethyl ether (100 ml) were added and the ethereal extract was washed with brine and dried over magnesium sulfate. Filtration and evaporation of the filtrate gave an oily residue, which was purified by flash column chromatography (silica; ethyl acetate) to afford the product as an amber solid (6.97 g).

Step b. 5-(4-bromobutyl)-2-(tert-butyldimethylsilyl)-1-(N,N-dimethylsulfamoyl)-imidazole. A solution of the product from step a (4.00 g, 14.5 mmol) in tetrahydrofuran (45 ml) was cooled under an atmosphere of argon to −78° C. n-Butyl lithium (1.5M in hexanes) (10.15 ml, 15.2 mmol) was added over 15 min and the solution stirred for a further 30 min. A solution of 1,4-dibromobutane (1.96 ml, 16.4 mmol) in tetrahydrofuran (5 ml) was added over 10 min. The solution was stirred for 30 min, allowed to warm to room temperature and stirred for 18 h. Saturated ammonium chloride solution (50 ml) and diethyl ether (50 ml) were added and the organic extract was washed with water and dried over magnesium sulfate. Filtration, evaporation of the filtrate and purification by flash column chromatography (silica, 20% ethyl acetate/hexane) afforded the product ($R_f$ 0.23) as a pale yellow crystalline solid (1.87 g): $^1$H NMR (300 MHz, CDCl$_3$) 6.97 (1H, s), 3.46 (2H, t), 2.84 (6H, s), 2.76 (2H, t), 2.00–1.78 (4H, m), 1.01 (9H, s), 0.39 (6H, s).

Step c. 4-[2-(tert-butyldimethylsilyl)-1-(N,N-dimethylsulfamoyl)imidazol-5-yl]butyl phenethyl sulfide. To a suspension of the product from step b (701 mg, 1.71 mmol) and potassium carbonate (283 mg, 2.05 mmol) in N,N-dimethylformamide (3 ml) was added phenethyl mercaptan (229 μl, 1.71 mmol). The reaction was stirred at room temperature for 6 h before the addition of brine (10 ml). The product was extracted with ethyl acetate (2×20 ml) and the combined organic material washed with water (3×20 ml) before drying over magnesium sulfate. Filtration and evaporation of the filtrate furnished the title compound as a pale yellow oil in quantitative yield: $^1$H NMR (300 MHz, CDCl$_3$) 7.33–7.20 (5H, m), 6.95 (1H, s), 2.98–2.70 (6H, m), 2.78 (6H, s), 2.58 (2H, t), 1.76–1.73 (4H, m), 1.01 (9H, s), 0.39 (6H, s).

Step d. A solution of the product from step c (883 mg, 1.89 mmol) in methanol (8 ml) at 0° C. was treated with a slurry of Oxone® (3.48 g, 5.66 mmol) in water (8 ml) portionwise and the resulting suspension stirred for 4.5 h at room temperature. The reaction was diluted with water, the product extracted with chloroform (3×30 ml) and the combined organic extracts washed with water and brine before drying over sodium sulfate. Filtration and evaporation of the filtrate gave a colourless oil which was heated at reflux in an ethanol (15 ml)/2M hydrochloric acid (8 ml) solution for 24 h. Solvent evaporation, treatment of the residue with methanolic ammonia and re-evaporation afforded a residue suitable for purification by flash column chromatography (silica, 1:10:90 ammonia(880)/methanol/dichloromethane). Thus, the title compound ($R_f$ 0.27) was isolated as a colourless oil (433 mg): $^1$H NMR (300 MHz, d$_4$-MeOH) 7.56 (1H, d), 7.34–7.23 (5H, m), 6.80 (1H, d), 3.37–3.32 (2H, m), 3.12–3.02 (4H, m), 2.61 (2H, t), 1.80–1.74 (4H, m). Found: C, 61.41; H, 6.97; N, 9.36%; C$_{15}$H$_{20}$N$_2$O$_2$S requires: C, 61.62; H, 6.89; N, 9.58%.

EXAMPLE 24

[4-(1H-Imidazol-4-yl)butyl] 4-chlorophenethyl sulfone

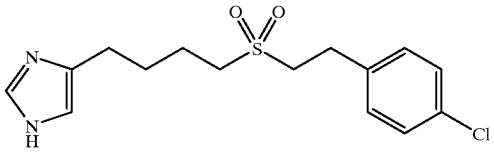

Step a. 1-chloro-2-(4-chlorophenyl)ethane. To a solution of 4-chlorophenethyl alcohol (5 ml, 37 mmol) and pyridine (3.0 ml, 37.0 mmol) in a two-necked flask, equipped with a dropping funnel and a reflux condenser fitted with calcium chloride drying tube, was added thionyl chloride (5.39 ml, 74.0 mmol) dropwise over 1 h. The reaction was heated at reflux for 1.5 h before being cooled in an ice-bath. This led to the precipitation of a white solid which was filtered off rapidly and washed with a small quantity of cold diethyl ether. The organic material was then washed cautiously with water (1×30 ml), 2N sodium hydroxide solution (2×30 ml) and water (1×30 ml), dried over magnesium sulfate, filtered and the solvent evaporated to give the desired product as a pale yellow oil (5.73 g): $^1$H NMR (300 MHz, CDCl$_3$) 7.29 (2H, d), 7.16 (2H, d), 3.70 (2H, t), 3.05 (2H, t).

Step b. S-(4-chlorophenethyl)isothiouronium chloride. A solution of the product from step a (4.98 g, 28.4 mmol) and thiourea (2.16 g, 28.4 mmol) in ethanol (35 ml) was heated at reflux for 22 h. Solvent evaporation and trituration of the resultant residue with diethyl ether afforded a solid which was isolated by fltration, washed with diethyl ether and dried in vacuo at 50° C. to furnish the product as a pale brown solid (5.42 g).

Step c. 4-chlorophenethyl thiol. The product from step b (500 mg, 2.0 mmol) was heated at reflux in a solution of sodium hydroxide (120 mg, 3.0 mmol) in water (2.5 ml) for 2 h. The reaction mixture was allowed to cool before acidification using dilute sulfuric acid and product extraction using diethyl ether (10 ml). The organic material was washed with water (2×20 ml), dried over sodium sulfate, filtered and the solvent evaporated to give the desired compound as a pale yellow oil (227 mg): $^1$H NMR (300 MHz, CDCl$_3$) 7.31–7.26 (2H, m), 7.15–7.10(2H, m), 2.94–2.88 (2H, m), 2.81–2.73 (2H, m), 1.37 (1H, t).

Step d. 5-(4-Bromobutyl)-2-(tert-butyldimethylsilyl)-1-(N,N-dimethylsulfamoyl)-imidazole (410 mg, 1.00 mmol) (Example 23, step b) was reacted with the product from step c (227 mg, 1.32 mmol) in essentially the same manner as the synthesis of Example 23, steps c and d to yield, after purification by flash column chromatography ($R_f$ 0.35, silica; 1:10:90 ammonia(880)/methanol/dichloromethane), the title compound as a white crystalline solid (41 mg): $^1$H NMR (300 MHz, d$_4$-MeOH) 7.57 (1H, dd), 7.32–7.25 (4H, m), 6.81 (1H, s), 3.34 (2H, m), 3.10–3.03 (4H, m), 2.62 (2H, m), 1.84–1.73 (4H, m). The maleate salt was prepared by lyophilisation of an equinmolar solution of the product and maleic acid in water/dioxan.

EXAMPLE 25

[4-(1H-Imidazol-4-yl)butyl]-4-chlorobenzyl sulfone

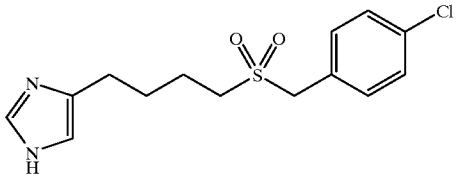

Step a. 4-[2-(tert-butyldimethylsilyl)-1-(N,N-dimethylsulfamoyl)imidazol-5-yl]butly 4-chlorobenzyl sulfide. 5-(4-Bromobutyl)-2-(tert-butyldimethylsilyl)-1-(N,N-dimethylsulfamoyl) imidazole (484 mg, 1.18 mmol) (Example 23, step b) and 4-chlorobenzyl mercaptan (156 μl, 1.18 mmol) were reacted together in a manner analogous to Example 23, step c to afford the desired compound as a pale yellow oil in quantative yield: $^1$H NMR (300 MHz, CDCl$_3$) 7.26 (4H, m), 6.93 (1H, s), 3.67 (2H, s), 2.81 (6H, s), 2.69 (2H, t), 2.44 (2H, t), 1.70 (4H, m), 1.00 (9H, s), 0.39 (6H, s).

Step b. A solution of the product from step a (599 mg, 1.23 mmol) was further reacted according to Example 23, step d to yield the title compound as a white crystalline solid (265 mg): $^1$H NMR (300 MHz, d$_4$-MeOH) 7.57 (1H, dd), 7.41 (4H, s), 6.79 (1H, s), 4.37 (2H, s), 3.00 (2H, dd), 2.62 (2H, t), 1.79–1.77 (4H, m).

EXAMPLE 26

[5-(1H-Imidazol-4-yl)pentyl] 4-chlorophenethyl sulfone

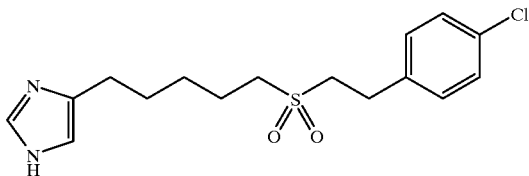

Step a. 5-(5-bromopenty)-2-(tert-butyldimethylsilyl)-1-(N,N-dimethylsulfamoyl) imidazole. The synthesis of this compound was achieved in an analogous fashion to that of Example 23, step b, employing 1,5-dibromopentane as the electrophilic reagent: $^1$H NMR (300 MHZ, CDCl$_3$) 6.95 (1H, s), 3.43 (2H, t), 2.84 (6H, s), 2.73 (2H, t), 1.95–1.90 (2H, m), 1.72–1.70 (2H, m), 1.59–1.57 (2H, m), 1.01 (9H, s), 0.39 (6H, s).

Step b. The product from step a (444 mg, 1.05 mmol) was reacted with 4-chlorophenethyl thiol (190 mg, 1.1 mmol) (Example 24, step c) according to the procedure for Example 23, step c. Subsequent oxidation and deprotection of the adduct was performed according to Example 23, step d to afford, after purification by flash column chromatography ($R_f$ 0.3, silica; 1:10:90 ammonia (880)/methanol/dichloromethane), the title compound as a white crystalline solid (25 mg): $^1$H NMR (300 MHz, d$_4$-MeOH) 7.54 (1H, d), 7.33–7.26 (4H, m), 6.77 (1H, s), 3.37–3.30 (2H, m), 3.11–2.99 (4H, m), 2.59 (2H, t), 1.80 (2H, quin.), 1.66 (2H, quin.), 1.45 (2H, quin.). The maleate salt was prepared by lyophilisation of an equimolar solution of the product and maleic acid in water/dioxan. Found: C, 52.62; H, 5.66; N, 6.24%; $C_{20}H_{25}ClN_2O_6S$ requires: C, 52.57; H, 5.51; N, 6.13%.

EXAMPLE 27

[5-(1H-Imidazol-4-yl)pentyl] 4-chlorobenzyl sulfone

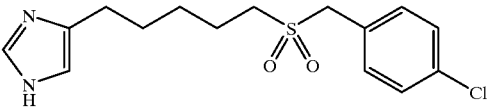

5-(5-Bromopentyl)-2-(tert-butyldimethylsilyl)-1-(N,N-dimethylsulfamoyl) imidazole (Example 26, step a) (385 mg, 0.91 mmol) was reacted with 4-chlorobenzyl mercaptan (126 μl, 0.95 mmol) in a manner analogous to Example 23, step c. The crude product was subjected to oxidation and deprotection according to the procedure for Example 23, step d. Purification of the adduct was achieved via preparative reverse phase hplc ($R_t$ 9.63 min; C$_{18}$; 40% acetonitrile/60% water+0.1% triethylamine) to give the title compound as a colourless oil (20 mg). $^1$H NMR (300 MHz, d$_4$-MeOH) 7.60 (1H, s), 7.40 (4H, m), 6.79 (1H, s), 4.38 (2H, s), 3.01 (2H, m), 2.59 (2H, t), 1.80 (2H, quin.), 1.66 (2H, quin.), 1.46 (2H, quin.). The maleate salt was prepared by lyophilisation of an equimolar solution of the product and maleic acid in water/dioxan. Found: C, 51.45; H, 5.19; N, 6.26%; $C_{19}H_{23}ClN_2O_6S$ requires: C, 51.52; H, 5.23; N, 6.32%.

EXAMPLE 28

N-(4-Fluorobenzyl)-5-(1H-imidazol-4-yl)-1-pentanesulfonamide

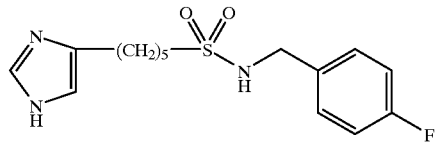

N-(tert-Butoxycarbonyl)-N-(4-fluorobenzyl)-methanesulfonamide was prepared from (4-fluorobenzyl) amine essentially according to the procedure of Example 1, steps a and b. It was reacted with 4-[1-(triphenylmethyl) imidazol-4-yl]butanal (Example 5, step c) according to the procedure of Example 5, step d to produce tert-butyl (1-((((4-fluorobenzyl)amino)sulfonyl)methyl)-4-(1-(triphenylmethyl)imidazol-4-yl)butyl) carbonate. This was converted to the title compound using essentially the procedure of Example 1, steps e to g. Thus, the title compound was isolated as a colourless oil: $^1$H NMR (300 MHz, CDCl$_3$) 7.52(1H, s), 7.33(2H, m), 7.04(2H, m), 6.76(1H, s), 4.27 (2H, s), 2.93(2H, t), 2.61(2H, t), 1.80(2H, quin.), 1.65(2H, quin.), 1.45(2H, quin.). The maleate salt was prepared by lyophilisation of an equimolar solution of the product and maleic acid in water/dioxan. Found: C, 51.50; H, 5.60; N, 9.41%; $C_{19}H_{24}FN_3O_6S$ requires: C, 51.69; H, 5.48; N, 9.52%.

EXAMPLE 29

N-(4-Methylbenzyl)-5-(1H-imidazol-4-yl)-1-pentanesulfonamide

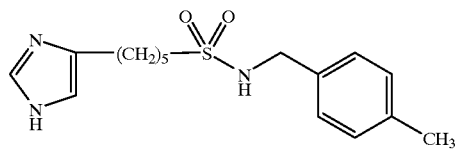

N-(tert-Butoxycarbonyl)-N-(4-methylbenzyl)-methanesulfonamide was prepared from (4-methylbenzyl)amine essentially according to the procedure of Example 1, steps a and b. It was reacted with 4-[1-(triphenylmethyl)imidazol-4-yl]butanal (Example 5, step c) according to the procedure of Example 5, step d to produce tert-butyl (1-((((4-methylbenzyl benzyl)amino)sulfonyl)methyl)-4-(1-(triphenylmethyl)imidazol4-yl)butyl) carbonate. This was converted to the title compound using essentially the procedure of Example 1, steps e to g. Thus, the title compound was isolated as a colourless oil: $^1$H NMR (300 MHz, $d_6$-DMSO) 11.70(1H, br s), 7.52(1H, t), 7.47(1H, s), 7.20 (2H, d), 7.12(2H, d), 6.68(1H, s), 4.06(2H, d), 2.83(2H, t), 2.43(2H, t), 1.60(2H, m), 1.49(2H, m), 1.27(2H, m). The maleate salt was prepared by lyophilisation of an equimolar solution of the product and maleic acid in water/dioxan. Found: C, 51.73; H, 6.44, N, 9.17%; $C_{19}H_{27}N_3O_6S.1.4H_2O$ requires:. C, 51.83; H, 6.50; N, 9.07%.

EXAMPLE 30

N-(4-Trifluoromethylbenzyl)-5-(1H-imidazol-4-yl)-1-pentanesulfonamide

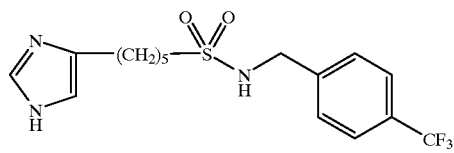

N-(tert-Butoxycarbonyl)-N-(4-trifluoromethylbenzyl)-methanesulfonamide was prepared from (4-trifluoromethylbenzyl)amine essentially according to the procedure of Example 1, steps a and b. It was reacted with 4-[1-(triphenylmethyl)imidazol-4-yl]butanal (Example 5, step c) according to the procedure of Example 5, step d to produce tert-butyl (1-((((4-trifluoromethylbenzyl)amino)sulfonyl)methyl)-4-(1-(triphenylmethyl)imidazol-4-yl)butyl) carbonate. This was converted to the title compound using essentially the procedure of Example 1, steps e to g. Thus, the title compound was isolated as a colourless oil: $^1$H NMR (300 MHz, $d_6$-DMSO) 7.71(2H, d), 7.56(2H, d), 7.51(1H, s), 6.71(1H, s), 4.23(2H, s), 2.95(2H, t), 2.45(2H, t), 1.63(2H, m), 1.53(2H, m), 1.34(2H, m). The maleate salt was prepared by lyophilisation of an equimolar solution of the product and maleic acid in water/dioxan. Found: C, 44.07; H, 5.29; N, 7.61%; $C_{20}H_{24}F_3N_3O_6S.2.8H_2O$ requires: C, 44.30; H, 5.51; N, 7.75%.

EXAMPLE 31

N-(1-Adamantylmethyl)-5-(1H-imidazol-4-yl)-1-pentanesulfonamide

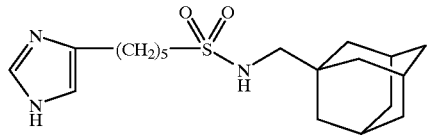

N-(tert-Butoxycarbonyl)-N-(1-adamantylmethyl)-methanesulfonamide was prepared from 1-adamantylmethylamine essentially according to the procedure of Example 1, steps a and b. It was reacted with 4-[1-(triphenylmethyl)imidazol-4-yl]butanal (Example 5, step c) according to the procedure of Example 5, step d to produce tert-butyl (1-adamantylmethyl)amino)sulfonyl)methyl)-4-(1-(triphenylmethyl)imidazol-4-yl)butyl) carbonate. This was converted to the title compound using essentially the procedure of Example 1, steps e to g. Thus, the title compound was isolated as a colourless oil: $^1$H NMR (300 MHz, $d_4$-MeOH) 7.56(1H, d), 6.77(1H, s), 3.01(2H, m), 2.67(2H, m), 2.60(2H, m), 1.97(3H, br s), 1.72(10H, m), 1.50(8H, m). The maleate salt was prepared by lyophilisation of an equimolar solution of the product and maleic acid in water/dioxan. Found: C, 57.07; H, 7.47; N, 8.51%; $C_{23}H_{35}N_3O_6S$ requires: C, 57.36; H, 7.35; N, 8.73%.

EXAMPLE 32

(E)-N-(4-Chlorobenzyl)-5-(1H-imidazol-4-yl)-1-pent-1-enesulfonamide

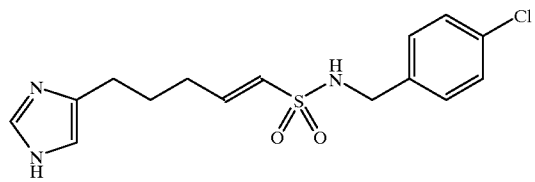

(E)-N-(4-Chlorobenzyl)-5-(1-(triphenylmethyl)imidazol-4-yl)-1-pent-1-enesulfonamide (Example 5, step e) (100 mg, 0.17 mmol) was deprotected and purified according to the procedure of Example 1, step g and the title compound ($R_f$ 0.30, 1:10:90 ammonia(880)/methanol/dichloromethane) was isolated as a colourless oil (47 mg, 80%): $^1$H NMR (300 MHz, $CDCl_3$) 7.54(1H, s), 7.28(4H, m), 6.76(1H, s), 6.70 (1H, m), 6.12(1H, d, J=15 Hz), 4.15(2H, s), 2.61(2H, m), 2.23(2H, m), 1.78(2H, m). The maleate salt was prepared by lyophilisation of an equimolar solution of the product and maleic acid in water/dioxan. Found: C, 51.55; H, 5.32; N, 9.26%, $C_{19}H_{22}ClN_3O_6S$ requires: C, 51.55; H, 4.86; N, 9.22%.

EXAMPLE 33

(E)-N-(4-Chlorobenzyl)-5-(1H-imidazol-4-yl)-1-pent-2-enesulfonamide

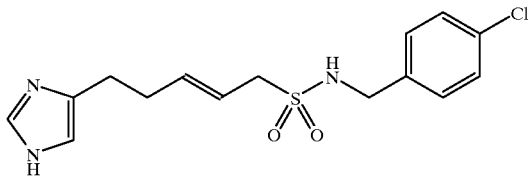

Step a. (E)-N-(4-chlorobenzyl)-5-(1-(triphenylmethyl)imidazol-4-yl)-1-pent-2-enesulfonamide. A solution of N-(tert-butoxycarbonyl)-N-(4-chlorobenzyl)-methanesulfonamide (Example 1, step b) (640 mg, 2.00 mmol) in THF (10 ml) was cooled to −78° C., 1M potassium t-butoxide (4.00 ml, 4.00 mmol) was added dropwise and the solution was stirred for 1 h. A solution of 4-[1-(triphenylmethyl)imidazol-4-yl]butanal (Example 5, step c) (760 mg, 2.00 mmol) in THF (10 ml) was added by means of a cannula. The mixture was stirred overnight, allowing it to warm slowly to room temperature. The reaction mixture was quenched with saturated ammonium chloride solution and extracted with ethyl acetate. The combined extracts were washed with brine, dried over magnesium sulfate, filtered and the solvent evaporated. Flash column chromatography (silica, 20% ethyl acetate/dichloromethane) of the residue gave the product as a colourless oil (161 mg, 12%).

Step b. The product from the previous step was deprotected and purified according to the procedure of Example 1, step g and the title compound ($R_f$ 0.40, 1:10:90 ammonia (880)/methanol/dichloromethane) was isolated as a colourless oil: $^1$H NMR (300 MHz, CDCl$_3$) 7.31(4H, m), 7.22(1H, s), 6.70(1H, s), 5.61(1H, dt, J=14.4, 7.2 Hz), 5.30(1H, dt, J=14.4, 7.5 Hz), 4.26(2H, s), 3.54(2H, d, J=7.5 Hz), 2.65 (2H, m), 2.32(2H, m). The maleate salt was prepared by lyophilisation of an equimolar solution of the product and maleic acid in water/dioxan. Found: C, 48.88; H, 5.78; N, 8.27%; $C_{19}H_{22}ClN_3O_6S.1.0H_2O$ requires: C, 49.02; H, 5.76; N, 8.57%.

EXAMPLE 34

N-(4-Chlorobenzyl)-N-methyl-5-(1H-imidazol-4-yl)-1-pentanesulfonamide

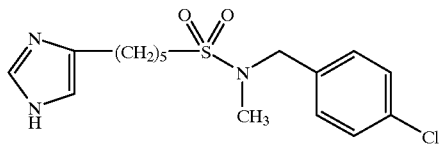

Step a. (E)-N-(4-chlorobenzyl)-N-methyl-5-(1-(triphenylmethyl)imidazol-4-yl)-1-pent-1-enesulfonamide. A suspension of (E)-N-(4-chlorobenzyl)-5-(1-(triphenylmethyl)imidazol-4-yl)-1-pent-1-enesulfonamide (Example 5, step e) (297 mg, 0.51 mmol) in dry dimethylformamide (1.7 ml) was cooled in ice. Sodium hydride (60% dispersion in oil) (22 mg, 0.56 mmol) was added, the cold bath was removed and the mixture was stirred for 1 h, giving a solution. Iodomethane (48 µl, 0.77 mmol) was added and stirring was continued overnight. The reaction was quenched with water (10 ml) and extracted with DCM (3×5 ml). The combined extracts were evaporated and the residue taken up in ethyl acetate (10 ml). The solution was washed four times with brine, dried over sodium sulfate, filtered and the solvent evaporated. Flash column chromatography (silica, 50% ethyl acetate/toluene) of the residue gave the product as a yellow oil (174 mg, 57%).

Step b. N-(4-chorobenzyl)-N-methyl-5-(1-(triphenylmethyl)imidazol-4-yl)-1-pentanesulfonamide. A round bottom flask containing the product from the previous step (174 mg, 0.29 mmol), 10% palladium-on-charcoal (18 mg) and THF (17 ml) was evacuated and flushed with hydrogen three times. The mixture was vigorously stirred overnight under an atmosphere of hydrogen. The catalyst was removed by filtration and the filtrate evaporated to give the product as a colourless oil (155 mg, 89%).

Step c. Trifluoroacetic acid (2 ml) was added to the product from the previous step (155 mg, 0.26 mmol). The flask was stoppered and the resultant yellow solution left to stand overnight under ambient conditions. The solvent was evaporated and the residue purified by flash column chromatography (silica; 1:10:90 anmuonia(880)/methanol/dichloromethane). Thus, the title compound ($R_f$ 0.35) was isolated as a colourless oil (83 mg, 90%): $^1$H NMR (300 MHz, d$_4$-MeOH) 7.56(1H, s), 7.35(4H, s), 6.78(1H, s), 4.30(2H, s), 3.08(2H, m), 2.73(3H, s), 2.60(2H, t), 1.81(2H, quin.), 1.68(2H, quin.), 1.49(2H, quin.). The maleate salt was prepared by lyophilisation of an equimolar solution of the product and maleic acid in water/dioxan. Found: C, 51.08; H, 5.60; N, 8.92%; $C_{20}H_{26}ClN_3O_6S$ requires: C, 50.90; H, 5.55, N, 8.90%.

EXAMPLE 35

N-(4-Chlorobenzyl)-N-(3-aminopropyl)-5-(1H-imidazol-4-yl)-1-pentanesulfonamide

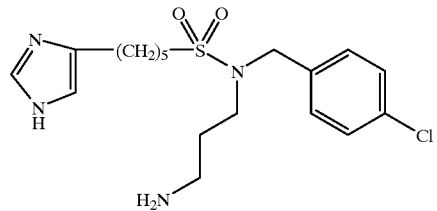

Step a. (E)-N-(4-chlorobenzyl)-N-(3-(1,3-dioxo-1,3-dihydro-isoindol-2-yl)-propyl)-5-(1-(triphenylmethyl) imidazol-4-yl)-1-pent-1-enesulfonamide. A solution of (E)-N-(4-chlorobenzyl)-5-(1-(triphenylmethyl)imidazol-4-yl)-1-pent-1-enesulfonamide (Example 5, step e) (212 mg, 0.36 mmol) in dry dimethylformamide (2 ml) was cooled in ice. Sodium hydride (60% dispersion in oil) (16 mg, 0.40 mmol) was added, the cold bath was removed and the mixture was stirred for 30 min, giving a solution. N-(3-bromopropyl) phthalimide (48 µl. 0.77 mmol) was added and the solution was heated at 80° C. overnight. The reaction was quenched with water (10 ml) and extracted with DCM (3×5 ml). The combined extracts were evaporated and the residue taken up in ethyl acetate (10 ml). The solution was washed four times with brine, dried over sodium sulfate, filtered and the solvent evaporated. Flash column chromatography (silica, 50% ethyl acetate/toluene) of the residue gave the product as a colourless oil (147 mg, 53%).

Step b. N-(4-chlorobenzyl)-N-(3-(1,3-dioxo-1,3-dihydro-isoindol-2-yl)-propyl)-5-(1-(triphenylmethyl)imidaol-4-yl)-1-pentanesulfonamide. A round bottom flask containing the product from the previous step (147 mg, 0.19 mmol), 10% palladium-on-charcoal (12 mg) and THF (15 ml) was evacuated and flushed with hydrogen three times. The mixture was vigorously stirred overnight under an atmosphere of hydrogen. The catalyst was removed by filtration and the filtrate evaporated to give the product as a colourless oil (57 mg, 39%).

Step c. N-(4-chlorobenzyl)-N-(3-aminopropyl)-5-(1-(triphenylmethyl)imidazol-4-yl)-1-pentanesulfonamide. A solution of the product from the previous step (57 mg, 0.071 mmol) and hydrazine hydrate (20 μl, 0.36 mmol) in ethanol (1 ml) was heated at reflux for 2 h. The precipitate was removed by filtration and the filtrate evaporated. The residue was extraced by trituration with chloroform. The extract was evaporated to give the product as a colourless oil in quantitative yield.

Step d. Trifluoroacetic acid (0.5 ml) was added to the product from the previous step. The flask was stoppered and the resultant yellow solution left to stand overnight under ambient conditions. The solvent was evaporated and the residue purified by flash column chromatography (silica; 2:20:80 ammonia(880)/methanol/dichloromethane). Thus, the title compound ($R_f$ 0.50) was isolated as a colourless oil (11 mg, 43%): $^1$H NMR (300 MHz, $d_4$-MeOH) 7.55(1H, s), 7.41(2H, d), 7.36(2H, d), 6.77(1H, s), 4.39(2H, s), 3.28(2H, t), 3.06(2H, m), 2.59(4H, dd), 1.80(2H, m), 1.70(2H, m), 1.57(2H, m), 1.47(2H, m).

EXAMPLE 36

N-Benzyl-N-(4-chlorobenzyl)-5-(1H-imidazol-4-yl)-1-pentanesulfonamide

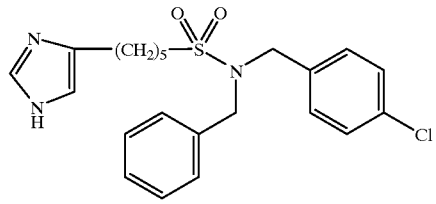

Step a. N-benzyl-N-(4-chlorobenzyl)-5-(1-(triphenylmethyl)imidazol-4-yl)-1-pentanesulfonamide. A solution of N-benzyl-5-(1-(triphenylmethyl)imidazol-4-yl)-1-pentanesulfonamide (see Example 13) (155 mg, 0.28 mmol) in THF (2 ml) was cooled to −78° C. and 1.5M lithium diisopropylamide (380 μl, 0.56 mmol) was added dropwise. The solution was stirred at 0° C. for 1 h and a solution of 4-chlorobenzyl bromide (58 mg, 0.28 mmol) in THF (1 ml) was added by means of a cannula. The cold bath was removed and the mixture was stirred overnight. The reaction was quenched by the addition of saturated ammonium chloride solution (10 ml) and the mixture was extracted with ethyl acetate (10 ml). The organic phase was washed with water and brine and dried over sodium sulfate. Flash column chromatography (silica, ethyl acetate) gave the product as a colourless oil (100 mg, 53%).

Step b. Trifluoroacetic acid (2 ml) was added to the product from the previous step (100 mg, 0.15 mmol). The flask was stoppered and the resultant yellow solution left to stand overnight under ambient conditions. The solvent was evaporated and the residue purified by flash column chromatography (silica; 1:10:90 ammonia(880)/methanol/dichloromethane). Thus, the title compound ($R_f$ 0.40) was isolated as a colourless oil (41 mg, 64%): $^1$H NMR (300 MHz, $d_4$-MeOH) 7.56(1H, s), 7.25(9H, m), 6.77(1H, s), 4.35(4H, s), 3.01(2H, m), 2.58(2H, t), 1.77(2H, quin,), 1.63(2H, quin.), 1.42(2H, quin.). The maleate salt was prepared by lyophilisation of an equimolar solution of the product and maleic acid in water/dioxan. Found: C, 56.69; H, 5.65; N, 7.85%; $C_{26}H_{30}ClN_3O_6S$ requires: C, 56.98; H, 5.52; N, 7.67%.

EXAMPLE 37

N-(4-Chlorobenzyl)-2-nitromethyl-5-(1H-imidazol-4-yl)-1-pentanesulfonamide

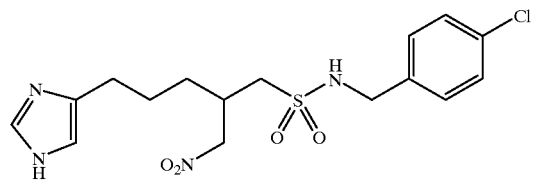

Step a. N-(4chlorobenzyl)-2-nitromethyl-5-(1-(triphenylmethyl)imidazol-4-yl)-1-pentanesulfonamide. To a mixture of (E)-N-(4-chlorobenzyl)-5-(1-(triphenylmethyl)imidazol-4-yl)-1-pent-1-enesulfonamide (Example 5, step e) (291 mg, 0.50 mmol), nitromethane (5 ml) and THF (5 ml) was added [2.2.2]-diazabicylcoundecene (224 μl, 1.50 mmol). The solution was heated at reflux for 2 h, allowed to cool and the solvent evaporated. The residue was purified by flash column chromatography (silica, 5% methanol/DCM) to give the product as a white solid (281 mg, 87%).

Step b. Trifluoroacetic acid (2 ml) was added to the product from the previous step (150 mg, 0.23 mmol). The flask was stoppered and the resultant yellow solution left to stand overnight under ambient conditions. The solvent was evaporated and the residue purified by flash column chromatography (silica, 1:10:90 ammonia(880)/methanol/dichloromethane). Thus, the title compound ($R_f$ 0.40) was isolated as a colourless oil (82 mg, 87%): $^1$H NMR (300 MHz, CDCl$_3$) 7.42(1H, s), 7.32(4H, m), 6.75(1H, s), 4.55 (2H, ddd), 4.28(2H, s), 3.16(1H, dd), 3.00(1H, dd), 2.73(1H, m), 2.60(2H, t), 1.65(3H, m), 1.47(1H, m). The maleate salt was prepared by lyophilisation of an equimolar solution of the product and maleic acid in water/dioxan. Found: C, 46.28; H, 4,93; N, 10.57%; $C_{20}H_{25}ClN_4O_8S$ requires: C, 46.47; H, 4.88; N, 10.84%.

EXAMPLE 38

2-Aminomethyl-N-(4-chlorobenzyl)-5-(1H-imidazol-4-yl)-1-pentanesulfonamide

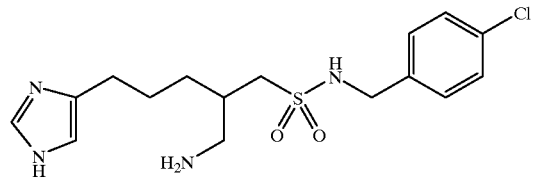

Step a. 2-aminomethyl-N-(4-chlorobenzyl)-5-(1-(triphenylmethyl)imidazol-4-yl)-1-pentanesulfonamide. A round bottom flask containing N-(4-chlorobenzyl)-2-nitromethyl-5-(1-(triphenylmethyl)imidazol-4-yl)-1-pentanesulfonamide (Example 37, step a) (260 mg, 0.41 mmol), Raney nickel (20 mg) and THF (10 ml) was evacuated and flushed with hydrogen three times. The mixture was vigorously stirred overnight under an atmosphere of hydrogen. The catalyst was removed by filtration through Celite and the residue washed with 50% methanol/DCM. The filtrate was evaporated and the residue purified by flash column chromatography (silica, 1:10:90 ammonia(880)/methanol/dichloromethane) to give the product as a white solid (155 mg, 62%).

Step b. A mixture of the product from the previous step (155 mg, 0.25 mmol), ethanol (5 ml) and 2M hydrochloric acid (1 ml) was heated at reflux for 1.5 h. The solvent was evaporated and residual hydrochloric acid was removed by co-evaporation with ethanol (2×10 ml). The residue was taken up in a little ethanol and the product was precipitated by the addition of diethyl ether. The precipitate was collected by filtration and dried in vacuo over phosphorus pentoxide. Thus the dihydrochloride salt of the title compound was obtained as a white solid (80 mg, 72%): $^1$H NMR (300 MHz, $d_6$-DMSO) 9.00(1H, s), 8.21(3H, br s), 7.88(1H, t), 7.39(5H, m), 4.18(2H, m), 3.36(1H, m), 3.01(2H, m), 2.85 (1H, m), 2.63(2H, t), 2.15(1H, m), 1.70(2H, m), 1.42 (2H, m). Found: C, 40.09; H, 5.93, N, 11.42%, $C_{16}H_{25}Cl_3N_4O_2S.2.0H_2O$ requires: C, 40.05; H, 6.09, N, 11.68%.

EXAMPLE 39

N-(4-Chlorobenzyl)-2-methylamino-5-(1H-imidazol-4-yl)-1-pentanesulfonamide

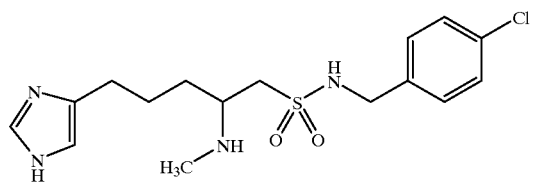

Step a. N-(4-chlorobenzy)-2-methylamino-5-(1-(triphenylmethyl)imidazol-4-yl)-1-pentanesulfonamide. A mixture of (E)-N-(4-chlorobenzyl)-5-(1-(triphenylmethyl) imidazol-4-yl)-1-pent-1-enesulfonamide (Example 5, step e) (291 mg, 0.50 mmol), 33% methylamine in industrial methylated spirit (5 ml) and THF (5 ml) was sealed in a Teflon-lined pressure vessel and heated at 80° C. for 5 h. The solution was allowed to cool and the solvent evaporated. The residue was purified by flash column chromatography (silica, 5% methanol/DCM then 1:10:90 ammonia(880)/methanol/dichloromethane) to give the product as a white solid (213 mg, 69%).

Step b. A mixture of th e product from the previous step (213 mg, 0.35 mmol), ethanol (5 ml) and 2M hydrochloric acid (1 ml) was heated at reflux for 2 h. The solvent was evaporated and residual hydrochloric acid was removed by co-evaporation with ethanol (2×10 ml). The residue was taken up in a little ethanol and the product was precipitated by the addition of diethyl ether. The precipitate was collected by filtration and dried in vacuo over phosphorus pentoxide. Thus the dihydrochloride salt of the title compound as obtained as a white solid (123 mg, 79%): 1H NMR (300 MHz, $d_6$-DMSO) 9.00(1H, d), 8.18(1H, t), 7.39(5H, m), 4.21(2H, m), 3.62(1H, m), 3.45(2H, m), 2.67(2H, m), 2.56(3H, s), 1.80(2H, m). Found: C, 41.66; H, 5.84; N, 12.21%; $C_{16}H_{25}Cl_3N_4O_2S.1.0H_2O$ requires: C, 41.61; H, 5.89; N, 12.13%.

EXAMPLE 40

2-Amino-N-(4-chlorobenzyl)-5-(1H-imidazol-4-yl)-1-pentanesulfonamide

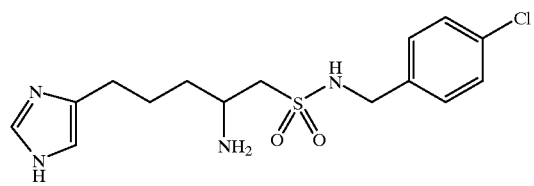

A mixture of (E)-N-(4-chlorobenzyl)-5-(1-(triphenylmethyl)imidazol-4-yl)-1-pent-1-enesulfonamide (Example 5, step e) (290 mg, 0.50 mmol), ethanol saturated with ammonia (10 ml) and THF (10 ml) was sealed in a Teflon-lined pressure vessel and heated at 120° C. overnight. The solution was allowed to cool and the solvent evaporated. The residue was purified by flash column chromatography (silica, 1:10:90 ammonia(880)/methanol/dichloromethane) to give the title compound was obtained as a white solid (123 mg, 79%): $^1$H NMR (300 MHz, $d_6$-DMSO) 7.92(1H, br s), 7.61(1H, d), 7.41(4H, m), 6.58(1H, d), 4.54(1H, m), 4.21 (2H, s), 3.65(1H, dd), 3.50(1H, dd), 3.29(2H, s), 2.67(2H, m), 2.65(2H, t), 2.10(1H, m), 1.95(1H, m), 1.81(1H, m), 1.66(1H, m). Found: C, 50.17; H, 5.99; N, 15.48%; $C_{15}H_{21}ClN_4O_2S$ requires: C, 50.48; H, 5.93; N, 15.70%.

EXAMPLE 41

(E,E)-N-(4-Chlorobenzyl)-4-(1H-imidazol-4-yl)-1-but-1,3-dienesulfonamide

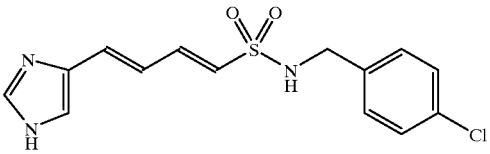

Step a. 3-[1-(triphenylmethyl)imidazol-4-yl]prop-2-en-1-al. A mixture of manganese dioxide (2.50 g, 28.8 mmol), 3-[1-(triphenylmethyl)imidazol-4-yl]prop-2-en-1-ol (1.06 g, 2.88 mmol)$^4$ and chloroform was heated at reflux for 2.5 h. The solid residues were removed by filtration and the filtrate evaporated to afford the product as a white solid (759 mg, 72%).

Step b. (E,E)-N-(4-chlorobenzyl)-4-(1-(triphenylmethyl) imidazol-4-yl)-1-but-1,3-enesulfonamide. A solution of N-(tert-butoxycarbonyl)-N-(4-chlorobenzyl)-methanesulfonamide (Example 1, step b) (658 mg, 2.06 mmol) in THF (5 ml) was cooled to −78° C., 1.5M lithium diisopropylamide (1.37 ml, 2.06 mmol) was added dropwise and the solution was stirred for 1 h. A solution of the product from the previous step (750 mg, 2.06 mmol) was added by means of a cannula and the solution was stirred overnight, allowing it to warm slowly to room temperature. The reaction mixture was partitioned between saturated ammonium chloride solution (20 ml) and ethyl acetate (20 ml). The aqueous phase was extracted with ethyl acetate (20 ml). The combined extracts were washed with brine, dried over magnesium sulfate, filtered and the solvent evaporated. Flash column chromatography (silica, 10–50% ethyl acetate/DCM) of the residue gave the product as a pale yellow solid (132 mg, 11%).

Step c. Trifluoroacetic acid (2 ml) was added to the product from the previous step (100 mg, 0.15 mmol). The flask was stoppered and the resultant yellow solution left to stand overnight under ambient conditions. The solvent was evaporated and the residue purified by flash column chromatography (silica; 1:10:90 ammonia(880)/methanol/ dichloromethane). Thus, the title compound ($R_f$ 0.30) was isolated as a colourless oil (54 mg, 73%): $^1$H NMR (300 MHz, d$_4$-MeOH) 7.74(1H, s), 7.32(4H, m), 7.27(1H, s), 7.11(1H, dd, J=14.7, 10.5 Hz), 6.90(1H, d, J=15.6 Hz), 6.78(1H, dd, J=15.3, 10.5 Hz), 6.34(1H, d, J=14.7 Hz), 4.13(2H, s). The maleate salt was prepared by lyophilisation of an equimolar solution of the product and maleic acid in water/dioxan. Found: C, 49.09; H, 4.16; N, 9.60%; $C_{18}H_{18}ClN_3O_6S$ requires: C, 49.15; H, 4.12; N, 9.55%.

EXAMPLE 42

2-(4-Chlorohenzyl)-5-(1H-imidazol-4-yl)-2,3,3a, 4, 5,7a-hexahydro-benzo[d]isothiazole 1,1-dioxide

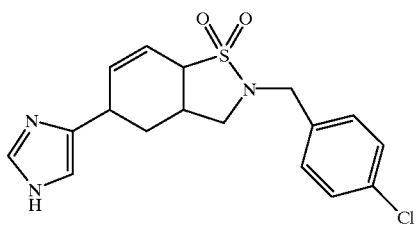

Step a. methyl 3-[1-(dimethylsulfamoyl)-imidazol-4-yl] propenoate. To a mixture of methyl 3-[1H-imidazol-4-yl] propenoate hydrochloride salt (16.1 g, 85.0 mmol),$^4$ triethylamine (37.5 ml, 269 mmol) and DCM (300 ml) was added dimethylsulfamoyl chloride (10 ml, 93.1 mmol). The solution was heated at reflux overnight, allowed to cool to room temperature, washed with water and brine and dried over magnesium sulfate. Filtration and evaporation afforded a yellow solid, which was recrystallised from isopropanol to give the product as a white solid (17.3 g, 78%).

Step b. 3-[1-(dimethylsulfamoyl)-imidazol-4-yl]prop-2-en-1-ol. A solution of the product from the previous step (1.00 g, 3.86 mmol) in THF (40 ml) was cooled to −15° C. (ice/methanol) and lithium aluminium hydride (77 mg, 1.93 mmol) was added in small portions over 15 min. The mixture was stirred at −15° C. for 1 h. Lithium aluminium hydride (24 mg, 0.64 mmol) was added in small portions over 10 min and mixture was stirred at −15° C. for 1 h. Without allowing the mixture to warm, the reaction was quenched by the addition of saturated ammonium chloride solution (10 ml). The organic phase was decanted and the inorganic residue was washed with diethyl ether (2×40 ml). The combined organic phases were washed with brine, dried over sodium sulfate, filtered and evaporated. The residue was purified by flash column chromatography (silica, 2% methanol/ethyl acetate) and the product was isolated as a white solid (220 mg, 25%).

Step c. 3-[1-(dimethylsulfamoyl)-imidazol-4-yl]propenal. A solution of oxalyl chloride (181 μl, 2.08 mmol) in DCM (6 ml) was cooled to −78° C. and dimethylsulfoxide (295 μl, 4.16 mmol) was added dropwise with concomitant effervescence. The solution was stirred for 10 min, by which time effervescence had ceased, and a solution of the product from the previous step (400 mg, 1.73 mmol) and dimethylsulfoxide (300 μl) in DCM (6 ml) was added by means of a cannula. The solution was stirred for 20 min, triethylamine (671 μl, 6.24 mmol) was added, the cold bath was removed and the resultant solution stirred for 1 h. A column of silica was pre-eluted with an equal volume of ethyl acetate until complete removal of solvent. The reaction mixture was applied to the top of the column and the column eluted to dryness. This was repeated with a column's volume of DCM to ensure complete removal of dimethylsulfide. The column was eluted with ethyl acetate and the aldehyde collected in fractions. Combination of the fractions and evaporation of the solvent gave the product as a white solid (368 mg, 93%).

Step d. (E,E)-N-(4-chlorobenzyl)-4-(1-(dimethylsulfamoyl)-imidazol-4-yl)-1-but-1,3-enesulfonamide. A solution of N-(tert-butoxycarbonyl)-N-(4-chlorobenzyl)-methanesulfonamide (Example 1, step b) (500 mg, 1.56 mmol) in THF (5 ml) was cooled to −78° C., 1M potassium t-butoxide (3.12 ml, 3.12 mmol) was added dropwise and the solution was stirred for 1 h. A solution of the product from the previous step (358 mg, 1.56 mmol) was added by means of a cannula and the solution was stirred overnight, allowing it to warm slowly to room temperature. The reaction mixture was partitioned between saturated ammonium chloride solution (20 ml) and ethyl acetate (20 ml). The organic phase was washed with brine, dried over magnesium sulfate, filtered and the solvent evaporated. Recrystallisation of the residue from ethyl acetate gave the product as a colourless crystalline solid (529 mg, 78%).

Step e. (E,E)-N-allyl-N-(4chlorobenzyl)-4-(1-(dimethylsulfamoyl)-imidazol-4-yl)-1-but-1,3-enesulfonamide. A solution of the product from the previous step (446 mg, 1.04 mmol) in dry dimethylformamide (3.6 ml) was cooled in ice. Sodium hydride (60% dispersion in oil) (47 mg, 1.18 mmol) was added, the cold bath was removed and the mixture was stirred for 25 min. The mixture was cooled again in ice, allyl bromide (139 μl, 1.61 mmol) was added and the solution was stirred overnight at ambient temperature. Water (15 ml) was added. The resultant precipitate was collected by filtration and dried in vacuo over phosphorus pentoxide. Recrystallization from ethanol afforded the product as a colourless crystalline solid (411 mg, 84%).

Step f. 2-(4-chlorobenzyl)-5-(1-(dimethylsulfamoyl)-imidazol-4-yl)-2,3,3a,4,5,7a-hexahydro-benzo[d] isothiazole 1,1-dioxide. A solution of the product from the previous step in dry degassed toluene (4 ml) was heated at 140–145° C. in a sealed pressure vessel for 48 h. The solvent was evaporated and the residue was recrystallised from ethanol to afford the product a white solid (28 mg, 58%).

Step g. A mixture of the product from the previous step (101 mg, 0.21 mmol), ethanol (1 ml) and 2M hydrochloric acid (1 ml) was heated at reflux overnight. The solvent was evaporated and the residue purified by flash column chromatography (silica; 1:10:90 ammonia(880)/methanol/ dichloromethane). Thus, the title compound ($R_f$ 0.30) was isolated as a white solid (44 mg, 58%). The product was a mixture of isomers (6:1) and the $^1$H NMR spectrum of the major isomer is reported: $^1$H NMR (300 MHz, d$_4$-MeOH) 7.60(1H, s), 7.34(4H, m), 6.84(1H, s), 6.32(1H, m), 5.90 (1H, m), 4.23(1H, d), 4.07(1H, d), 3.99(1H, m), 3.47(1H, m), 3.33(1H, m), 2.83(2H, m), 2.06(1H, m), 1.91(1H, m). The maleate salt was prepared by lyophilisation of an equimolar solution of the product and maleic acid in water/ dioxan. Found: C, 52.29; H, 4.70; N, 8.78%; $C_{21}H_{22}ClN_3O_6S$ requires: C, 52.55; H, 4.62; N, 8.76%.

REFERENCES

1. H. Stark, K. Purand, A. Hüls, X. Ligneau, M. Garbarg, J.-C. Schwartz, W. Schunack *J. Med. Chem.* 1996, 39, 1220.

2. J. L. Kelley, C. A. Miller, E. W. McLean *J. Med. Chem.* 1977, 20, 721.
3. R. C. Vollinga, W. M. P. B. Mange, R. Leurs, H. Timmerman *J. Med. Chem.* 1995, 38, 266.
4. C. Sellier, A. Buschauer, S. Elz, W. Schunack *Liebigs Ann. Chem.* 1992, 317.
5. M. J. Tozer, A. J. A. Woolford, I. D. Linney *Synlett* 1998, 186.
6. M. E. Thompson, *J. Org. Chem.* 1984, 49, 1700.

The biological activity of the compounds of the examples was measured using the ileal longitudinal muscle, myenteric plexus assay described by Paton and Aboo Zar (*J. Physiol.* 1968, 194, 13–33). Male Dunkin-Hartley guinea pigs (250–300 g) were employed. Briefly, a 50 cm portion of ileum proximal to the caecum was removed, after discarding the terminal 20 cm. Ileal segments (3 cm) were cleaned by passing Krebs-Henseleit buffer containing 3 $\mu$M mepyramine gently through the ileum using a Pasteur pipette (size: 13.8 cm length, 0.65 cm diameter). To avoid unnecessary damage to the tissue, Krebs-Henseleit buffer was passed through the ileal segment, while it was lying horizontally on a petri dish. Therefore, the ileum was not over-distended and the buffer flowed through with ease. Each segment was then passed over a Pasteur pipette and the longitudinal muscle layer and adhering myenteric plexus was teased away using moist cotton wool, by stroking tangentially away from the mesenteric attachment. The tissues were suspended in 20 ml organ baths containing Krebs-Henseleit buffer at 37±1° C. and gassed with 95% $CO_2$/5% $O_2$. The tissues were ligated to two parallel stainless steel wires, situated between two platinum electrodes (0.76 cm length, 0.06 cm diameter). All measurements were recorded isometrically (Grass FTO3 transducer). Following an initial loading tension of 1 g, the tissues were stimulated with electrical pulses at a frequency of 0.1 Hz and a pulse duration of 0.5 msec, as described by Kosterlitz & Watt (*Br. J. Pharmacol.* 1968, 266–276). Initially, the tissues were stimulated at supramaximal (1.3 fold times maximal) voltage for a period of 30 min and then the tissues were washed and re-stimulated. A "sighter dose" of the selective histamine $H_3$-receptor agonist, R-($\alpha$)-methylhistamine (0.3 $\mu$M) (Arrang et al. *Nature*, 1987, 117–123), was administered. Upon generation of response, the "sighter dose" was removed from the tissues by "washout" (6 washes over 60 min) and during this period the electrical stimulation was switched off. The tissues were then re-stimulated and allowed to stabilise prior to the addition of drug treatments, which were allocated on a randomised block basis to the organ baths. Following the incubation period, a single cumulative E/[A] curve was obtained. The experimental E/[A] curve data was expressed as the percentage inhibition of the peak height of electrically-stimulated contraction. Antagonist affinity values were calculated from the degree of rightward shift of the R-($\alpha$)-methylhistamine E/[A] curves using Schild's methods (Arunlakshana & Schild *Br. J. Pharmacol.* 1959, 48–58). The results are set out in Table 1. Typical variance in this assay is ±0.15 log units.

TABLE 1

| Example No. | $pK_B$ (functional assay) - ileum |
| --- | --- |
| 1 | 8.06 |
| 2 | 6.62 |
| 3 | 7.90 |

TABLE 1-continued

| Example No. | $pK_B$ (functional assay) - ileum |
| --- | --- |
| 4 | 6.59 |
| 5 | 8.46 |
| 6 | 7.79 |
| 7 | 8.29 |
| 8 | 7.90 |
| 9 | 6.52 |
| 11 | 7.53 |
| 12 | 7.31 |
| 13 | 7.23 |
| 14 | 6.14 |
| 15 | 8.47 |
| 16 | 7.74 |
| 17 | 7.33 |
| 18 | 6.41 |
| 19 | 6.61 |
| 20 | 6.48 |
| 21 | 7.23 |
| 22 | 7.10 |
| 23 | 6.67 |
| 24 | 7.97 |
| 25 | 7.52 |
| 26 | 8.11 |
| 27 | 7.85 |
| 28 | 7.72 |
| 29 | 7.59 |
| 30 | 8.03 |
| 31 | 6.76 |
| 32 | 7.60 |
| 33 | 8.33 |
| 34 | 7.76 |
| 35 | 6.82 |
| 36 | 5.81 |
| 37 | 7.69 |
| 38 | 7.91 |
| 39 | 7.61 |
| 41 | 5.58 |
| 42 | 5.68 |

Histamine $H_3$ Radioligand Binding Assay—Guinea Pig Ileum

Preparation of Membranes

Male Dunkin Hartley guinea pigs (200–300 g) were used. The small intestine was rapidly removed (cut ~5 cm from caecum and 5 cm from stomach) and placed in ice-cold 20 mM Hepes-NaOH buffer (pH7.4 at 21±3° C.). The tissue was cut into ~10 cm segments, flushed through with ice-cold 20 mM Hepes-NaOH buffer and placed in a beaker containing fresh buffer at 4° C. 10 cm segments of ileum were threaded onto a glass pipette and the longitudinal muscle myenteric plexus was peeled away from the circular muscle using damp cotton-wool. Longitudinal muscle myenteric plexus was immediately placed in ice-cold Viaspan® solution (~100 ml for tissue from 3 guinea pigs) and placed in the refrigerator for 24 hours.

Pre-soaked tissue was weighed and minced with scissors. The tissue was then homogenised in Viaspan® using a polytron (Kinematica AG; PT-DA 3020/2TS, 3×~1–2 s). 50 ml of 500 mM Tris HCl (pH6.9 at 21±3° C.) was added to the tissue and the mixture centrifuged at 39,800×g for 12 min at 4° C. The supernatant was discarded and rehomogenised in 100 ml ice-cold 20 mM Hepes-NaOH buffer (pH7.4 at 21±3° C.) using a teflon-in-glass homogeniser (setting 10; 3×). The homogenate was recentrifuged at 39,800×g and the pellet resuspended in 20 mM Hepes-NaOH buffer (pH7.4 at 21±3° C.), to a tissue concentration of 50 mg.ml$^{-1}$, using a polytron (Brinkman, PT10, 3×~1 s).

Incubation Conditions

Guinea pig ileum longitudinal muscle myenteric plexus membranes (400 $\mu$l) were incubated for 165 min at 21±3° C.

in a final volume of 500 μl with 20 mM Hepes-NaOH buffer containing [$^3$H]-R-α-methylhistamine (50 μl; 3 nM) and competing compound. Total and non-specific binding of [$^3$H]-R-α-methylhistamine were defined using 50 μl of buffer and 50 μl of 10 μM thioperamide, respectively. The assay was terminated by rapid filtration through Whatman GF/B filters, presoaked (2 hr) in 0.1% polyethyleneimine, using a Brandell Cell Harvester. The filters were washed (3×3 ml) with ice-cold 50 mM Tris-HCl (pH6.9 at 21±3° C.), transferred into scintillation vials, 5 ml liquid scintillation cocktail was added and after 4 hours the bound radioactivity was determined by counting (4 min) in a Beckman liquid scintillation counter.

Data Analysis

Data are analysed using GraphPad prism and the general equation for a competition curve with variable Hill slope ($n_H$).

$$Y = \text{Non-specific binding} + \frac{(\text{Total binding} - \text{Non-specific binding})}{1 + 10^{((\log IC_{50} - X) \cdot n_H)}}$$

where

X is the log concentration of competing compound,

Y is the binding obtained at each concentration of X, $pIC_{50}$ is the concentration of the competitor required to compete for half of the specific binding.

The $IC_{50}$ is converted to the $K_I$ using the Cheng Prusoff equation, $$K_I = IC_{50}/(1+(L/K_D))$$

where $IC_{50}$ is the concentration of competitor required to compete for half the specific binding, L is the radioligand concentration used, $K_D$ is the equilibrium dissociation constant for the radioligand determined by saturation experiments.

The results are set out in Table 2. Typical variance in this assay is ±0.12 log units.

TABLE 2

| Example No. | pK$_I$ (binding assay) - ileum |
|---|---|
| 1 | 8.07 |
| 3 | 7.99 |
| 5 | 8.73 |
| 6 | 7.90 |
| 12 | 7.22 |
| 26 | 7.99 |
| 27 | 7.93 |

Histamine H$_3$ Radioligand Binding Assay—Guinea Pig Cortex

Preparation of Membranes

Male Dunkin Hartley guinea pigs (200–300 g) were used. The whole brain was removed and immediately placed in ice-cold 20 mM Hepes-NaOH buffer (pH7.4 at 21±3° C.). The cortex was dissected, weighed and homogenised in ice-cold 20 mM Hepes-NaOH buffer (pH7.4 at 21±3° C.) (50 ml/guinea-pig cortex) using a polytron (Kinematica AG; PT-DA 3020/2TS, 3×3 s). The homogenate was centrifuged at 100×g for 5 min and the supernatants pooled and stored at 4° C. The pellets were rehomogenised in fresh ice-cold buffer (80 ml) and recentrifuged (100×g for 5 min). The supernatants were pooled and pellets rehomogenised and recentrifuged (100×g for 5 min). All supernatants were pooled and centrifuged at 39,800×g for 12 min at 4° C. The final pellet was resuspended in 20 mM Hepes-NaOH buffer (pH7.4 at 21±3° C.) to a tissue concentration of 7.5 mg.ml$^{-1}$, using a teflon-in-glass homogeniser.

Incubation Conditions and Data Analysis

These were essentially identical to those used for the guinea pig ileum myenteric plexus assay described above, except that the final assay concentration of [$^3$H]-R-α-methylhistamine was 0.1 nM. The results are set out in Table 3. Typical variance in this assay is ±0.12 log units.

TABLE 3

| Example No. | pK$_I$ (binding assay) - cortex |
|---|---|
| 1 | 8.58 |
| 2 | 6.56 |
| 3 | 8.56 |
| 4 | 7.21 |
| 5 | 8.58 |
| 6 | 8.30 |
| 7 | 8.54 |
| 8 | 8.37 |
| 9 | 7.35 |
| 10 | 6.13 |
| 11 | 8.14 |
| 12 | 7.85 |
| 13 | 8.05 |
| 14 | 7.09 |
| 15 | 9.05 |
| 16 | 8.95 |
| 17 | 7.66 |
| 18 | 6.85 |
| 19 | 7.71 |
| 20 | 6.90 |
| 21 | 7.92 |
| 22 | 7.54 |
| 23 | 7.32 |
| 24 | 8.25 |
| 25 | 7.73 |
| 26 | 8.35 |
| 27 | 9.18 |
| 28 | 8.15 |
| 29 | 8.21 |
| 30 | 8.82 |
| 31 | 6.73 |
| 32 | 8.23 |
| 33 | 9.07 |
| 34 | 7.99 |
| 35 | 7.74 |
| 36 | 6.70 |
| 37 | 8.18 |
| 38 | 8.88 |
| 39 | 8.53 |
| 40 | 4.65 |
| 41 | 5.80 |
| 42 | 5.91 |

What is claimed is:

1. A compound of the formula

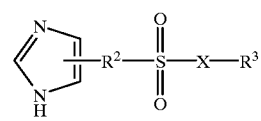

(I)

wherein

R$^2$ is C$_2$ to C$_8$ alkylene or alkenylene chain, optionally substituted by a hydroxyl group or an oxo group;

R$^3$ is C$_2$ to C$_{15}$ hydrocarbyl, in which one or more hydrogen atoms may be replaced by halogen atoms and up to 3 carbon atoms may be replaced by oxygen, nitrogen or sulfur atoms, provided that $R^3$ does not contain a —O—O— group;

X is —$NR^4$—, wherein $R^4$ is hydrogen or non-aromatic $C_1$ to $C_5$ hydrocarbyl, in which one or more hydrogen atoms may be replaced by hydrogen atoms and up to 2 carbon atoms may be replaced by oxygen, nitrogen or sulfur atoms, provided that $R^4$ does not contain a —O—O— group, or aryl($C_1$ to $C_3$)alkyl, or a pharmaceutically acceptable salt thereof.

2. A compound according to claim 1 wherein $R^3$ is cycloalkylalkyl or aryl($C_1$ to $C_3$)alkyl.

3. A compound according to claim 1 wherein $R^4$ is hydrogen, $C_1$ to $C_5$ alkyl or benzyl.

4. A pharmaceutical composition comprising a therapeutically effective amount of a compound according to claim 1, and a physiologically acceptable diluent or carrier.

* * * * *